US006426339B1

(12) United States Patent
Berde et al.

(10) Patent No.: US 6,426,339 B1
(45) Date of Patent: *Jul. 30, 2002

(54) FORMULATIONS AND METHODS FOR PROVIDING PROLONGED LOCAL ANESTHESIA

(75) Inventors: Charles B. Berde, Brookline; Robert S. Langer, Newton, both of MA (US); Joanne Curley, San Jose, CA (US); Jenny Castillo, Philadelphia, PA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/541,928

(22) Filed: Apr. 3, 2000

Related U.S. Application Data

(63) Continuation of application No. 08/714,783, filed on Sep. 16, 1996, now Pat. No. 6,046,187.

(51) Int. Cl.[7] ....................... A61K 31/56; A61K 31/445

(52) U.S. Cl. .................. 514/180; 514/330; 514/818

(58) Field of Search ................ 514/180, 330, 514/818

(56) References Cited

U.S. PATENT DOCUMENTS

| | | | |
|---|---|---|---|
| 2,174,796 A | 10/1939 | Luzzi | 32/34 |
| 2,835,628 A | 5/1958 | Saffir | 167/84 |
| 3,185,625 A | 5/1965 | Brown | 167/82 |
| 3,337,400 A | 8/1967 | Smith | 167/52 |
| 3,507,952 A | 4/1970 | Rednick et al. | 424/22 |
| 3,535,419 A | 10/1970 | Siegrist et al. | 424/22 |
| 3,736,646 A | 6/1973 | Schmitt et al. | 29/458 |
| 3,755,558 A | 8/1973 | Scribner | 424/47 |
| 3,773,919 A | 11/1973 | Boswell et al. | 424/19 |
| 3,844,285 A | 10/1974 | Laby | 128/260 |
| 3,887,699 A | 6/1975 | Yolles | 424/19 |
| 3,943,063 A | 3/1976 | Morishita et al. | 252/316 |
| 3,972,995 A | 8/1976 | Tsuk et al. | 424/28 |
| 3,972,999 A | 8/1976 | Tsuk | 424/78 |
| 3,976,071 A | 8/1976 | Sadek | 128/260 |
| 3,991,766 A | 11/1976 | Schmitt et al. | 128/335.5 |
| 4,001,388 A | 1/1977 | Shell | 424/14 |
| 4,011,312 A | 3/1977 | Reuter et al. | 424/78 |
| 4,034,758 A | 7/1977 | Theeuwes | 128/260 |
| 4,039,653 A | 8/1977 | DeFoney et al. | 424/19 |
| 4,070,347 A | 1/1978 | Schmitt | 260/77.5 D |
| 4,076,798 A | 2/1978 | Casey et al. | 424/22 |
| 4,089,800 A | 5/1978 | Temple | 252/316 |
| 4,093,709 A | 6/1978 | Choi et al. | 424/19 |
| 4,118,470 A | 10/1978 | Casey et al. | 424/19 |
| 4,131,648 A | 12/1978 | Choi et al. | 424/22 |
| 4,138,344 A | 2/1979 | Choi et al. | 252/1 |
| 4,144,317 A | 3/1979 | Higuchi et al. | 424/21 |
| 4,164,560 A | 8/1979 | Folkman et al. | 424/22 |
| 4,166,107 A | 8/1979 | Miller et al. | 424/19 |
| 4,166,800 A | 9/1979 | Fong | 252/316 |
| 4,175,326 A | 11/1979 | Goodson | 433/80 |
| 4,226,848 A | 10/1980 | Nagai et al. | 424/19 |
| 4,250,163 A | 2/1981 | Nagai et al. | 424/14 |
| 4,276,880 A | 7/1981 | Malmin | 128/221 |

(List continued on next page.)

FOREIGN PATENT DOCUMENTS

| | | | |
|---|---|---|---|
| CA | 1143289 | 3/1983 | A61K/9/50 |
| DE | 2930248 | 2/1981 | B01J/13/02 |
| EP | 0244118 | 11/1987 | A61K/9/10 |
| EP | 0430474 | 6/1991 | A61K/9/70 |
| GB | 2034182 | 6/1980 | A61K/9/00 |
| WO | 9207555 | 5/1992 | A61K/9/22 |
| WO | WO9215286 | 9/1992 | A61K/9/22 |
| WO | WO9320138 | 10/1993 | |
| WO | WO9405265 | 3/1994 | A61K/9/20 |
| WO | WO96/41616 | 12/1996 | A61K/9/14 |

OTHER PUBLICATIONS

Curley et al. "Prolonged regional nerve blockade: Injectable biodegradable bupivacaine/polyester microspheres" Anesthesiology 1996, 84(6), 1401–1410.*

Jaffe, Howard, "Microencapsulation Process", copy of government–owned invention description, serial No.: 943,940, filed Aug. 17, 1978, U.S. Department of Agriculture, Hyattsville, MD, 11 pages.

Algire, Glenn H., et al., "Vascular Reactions of Normal and Malignant Tissues In Vivo. VI.. The Role of Hypotension in the Action of Components of Podophyllin on Transplanted Sarcomas", *Journal of the American Cancer institute*, vol. 14, No. 4, Feb. 1954, pp. 879–893.

Baguley, Bruce C., et al., "Inhibition of Growth of Colon 38 Adenocarcinoma by Vinblastine and Colchicine: Evidence for a Vascular Mechanism", *Eur.J. Cancer*, vol. 27, No. 4, pp. 482–487 (1991).

Le Corre, P., et al., "In vitro controlled release kinetics of local anesthetics from poly(D,L–lactide) and poly ((lactide–co–glycolide) microspheres", *J. Microencapsulation* vol. 14, No. 2, pp. 243–255 (1997). (abstract).

Beck, Lee R., et al., "Poly(DL–Lactide–co–glycolide)/Norethisterone Microcapsules: an Injectable Biodegradable Contraceptive", *Biology of Reproduction*, vol. 28, pp. 186–195 (1983).

Bissery, M.C., et al., "A Study of Process Parameters in the Making of Microspheres by the Solvent Evaporation Procedure", EXPO–Congr. Int. Technol. Pharm., 3rd, pp. 233–239 (1983).

Bodmeier, R., et al., "Solvent selection in the preparation of poly(DL–lactide) microspheres prepared by the solvent evaporation method", *International Journal of Pharmaceutics*, vol. 43, pp. 179–186, (1988).

(List continued on next page.)

Primary Examiner—Theodore J. Criares
Assistant Examiner—Jennifer Kim
(74) *Attorney, Agent, or Firm*—Davidson, Davidson & Kappel, LLC

(57) ABSTRACT

The use of glucocorticosteroids in methods and formulations for prolonging and/or reactivating local anesthesia or local anesthesia previously induced by a local anesthetic agent, is disclosed.

65 Claims, 16 Drawing Sheets

U.S. PATENT DOCUMENTS

| | | | |
|---|---|---|---|
| 4,293,539 A | 10/1981 | Ludwig et al. | 424/19 |
| 4,321,038 A | 3/1982 | Porteous | 433/136 |
| 4,369,172 A | 1/1983 | Schor et al. | 424/19 |
| 4,384,975 A | 5/1983 | Fong | 427/213.36 |
| 4,389,330 A | 6/1983 | Tice et al. | 427/213.36 |
| 4,404,183 A | 9/1983 | Kawata et al. | 424/19 |
| 4,419,340 A | 12/1983 | Yolles | 424/19 |
| 4,434,153 A | 2/1984 | Urquhart et al. | 424/22 |
| 4,479,911 A | 10/1984 | Fong | 264/4.6 |
| 4,530,840 A | 7/1985 | Tice et al. | 514/179 |
| 4,542,025 A | 9/1985 | Tice et al. | 424/78 |
| 4,557,925 A | 12/1985 | Lindahl et al. | 424/19 |
| 4,568,535 A | 2/1986 | Loesche | 424/19 |
| 4,568,536 A | 2/1986 | Kronenthal et al. | 424/22 |
| 4,569,837 A | 2/1986 | Suzuki et al. | 424/28 |
| 4,585,651 A | 4/1986 | Beck et al. | 424/88 |
| 4,597,960 A | 7/1986 | Cohen | 424/28 |
| 4,622,219 A | 11/1986 | Haynes | 424/38 |
| 4,622,244 A | 11/1986 | Lapka et al. | 427/213.32 |
| 4,623,588 A | 11/1986 | Nuwayser et al. | 428/402.24 |
| 4,650,665 A | 3/1987 | Kronenthal et al. | 424/435 |
| 4,652,441 A | 3/1987 | Okada et al. | 424/19 |
| 4,685,883 A | 8/1987 | Jernberg | 433/136 |
| 4,713,244 A | 12/1987 | Bawa et al. | 424/429 |
| 4,716,203 A | 12/1987 | Casey et al. | 525/408 |
| 4,725,442 A | 2/1988 | Haynes | 424/490 |
| 4,735,945 A | 4/1988 | Sakamoto et al. | 514/279 |
| 4,756,907 A | 7/1988 | Beck et al. | 424/85 |
| 4,757,128 A | 7/1988 | Domb et al. | 528/271 |
| 4,767,628 A | 8/1988 | Hutchinson | 424/426 |
| 4,780,320 A | 10/1988 | Baker | 424/493 |
| 4,789,726 A | 12/1988 | Hutchinson | 528/354 |
| 4,801,739 A | 1/1989 | Franz et al. | 560/185 |
| 4,861,627 A | 8/1989 | Mathiowitz et al. | 427/213.31 |
| 4,874,612 A | 10/1989 | Deasy | 424/425 |
| 4,882,168 A | 11/1989 | Casey et al. | 424/468 |
| 4,883,666 A | 11/1989 | Sabel et al. | 424/422 |
| 4,888,176 A | 12/1989 | Langer et al. | 424/426 |
| 4,891,225 A | 1/1990 | Langer et al. | 424/428 |
| 4,892,736 A | 1/1990 | Goodson | 424/435 |
| 4,906,474 A | 3/1990 | Langer et al. | 424/428 |
| 4,919,939 A | 4/1990 | Baker | 424/493 |
| 4,933,182 A | 6/1990 | Higashi et al. | 424/425 |
| 5,000,886 A | 3/1991 | Lawter et al. | 264/4.3 |
| 5,004,602 A | 4/1991 | Hutchinson | 424/78 |
| 5,007,790 A | 4/1991 | Shell | 424/451 |
| 5,013,553 A | 5/1991 | Southard et al. | 424/426 |
| 5,019,379 A | 5/1991 | Domb et al. | 424/78 |
| 5,019,400 A | 5/1991 | Gombotz et al. | 424/497 |
| 5,032,384 A | 7/1991 | Yeh et al. | 424/49 |
| 5,061,492 A | 10/1991 | Okada et al. | 424/423 |
| 5,075,109 A | 12/1991 | Tice et al. | 424/88 |
| 5,084,267 A | 1/1992 | Damani | 424/426 |
| 5,100,669 A | 3/1992 | Hyon et al. | 424/426 |
| 5,114,718 A | 5/1992 | Damani | 424/422 |
| 5,122,367 A | 6/1992 | Ron et al. | 424/80 |
| 5,143,661 A | 9/1992 | Lawter et al. | 264/4.3 |
| 5,188,837 A | 2/1993 | Domb | 424/450 |
| 5,198,220 A | 3/1993 | Damani | 424/426 |
| 5,222,529 A | 6/1993 | Zoltan | 141/4 |
| 5,225,441 A | 7/1993 | Vogel et al. | 514/557 |
| 5,227,165 A | 7/1993 | Domb et al. | 424/450 |
| 5,236,355 A | 8/1993 | Brizzolara et al. | 433/80 |
| 5,244,678 A | 9/1993 | Legros et al. | 424/450 |
| 5,252,701 A | 10/1993 | Jarrett et al. | 528/354 |
| 5,264,207 A | 11/1993 | Bommelaer et al. | 424/69 |
| 5,272,139 A | 12/1993 | Cary, Jr. | 514/171 |
| 5,292,512 A | 3/1994 | Schaefer | 424/401 |
| 5,330,452 A | 7/1994 | Zook | 604/307 |
| 5,401,507 A | 3/1995 | Lewis | 424/426 |
| 5,407,609 A | 4/1995 | Tice et al. | 264/46 |
| 5,492,901 A | 2/1996 | Fabunan | 514/171 |
| 5,540,912 A | 7/1996 | Roorda et al. | 424/422 |
| 5,543,156 A | 8/1996 | Roorda et al. | 424/484 |
| 5,618,563 A | 4/1997 | Berde et al. | 424/501 |
| 5,650,173 A | 7/1997 | Ramstack et al. | 424/489 |
| 5,654,008 A | 8/1997 | Herbert et al. | 424/489 |
| 5,700,485 A | 12/1997 | Berde et al. | 424/501 |
| 5,922,340 A | 7/1999 | Berde et al. | 424/426 |
| 6,046,187 A * | 4/2000 | Berde et al. | 514/180 |
| 6,162,462 A | 12/2000 | Bolotin et al. | 424/450 |
| 6,197,326 B1 | 3/2001 | Suzuki et al. | 424/426 |
| 6,238,702 B1 * | 5/2001 | Berde et al. | 514/180 |

OTHER PUBLICATIONS

Bodmeier, R., et al., "Polylactic acid microspheres containing quinidine base and quinidine sulphate prepared by the solvent evaporation technique. II. Some process parameters influencing the preparation and properties of microspheres", *J. Microencapsulation*, vol. 4, No. 4, pp. 289–297 (1987).

Hill, S.A., et al., "Vinca Alkaloids: Anti–vascular Effects in a Murine Tumour", *Euro. J. Cancer*, vol. 29A, No. 9, pp. 1320–1324 (1993).

Jalil, R., et al., "Microencapsulation using poly(L–lactic acid) I: Microcapsule properties affected by the preparative technique", *J. Microencapsul.*, vol. 6, No. 4, pp. 473–484 (Oct.–Dec.) (1989).

Lin, Shan–Yang, et al., "Insulin Controlled–release Microcapsules to Prolong the Hypoglycemic Effect in Diabetic Rats", *Biomat. Art. Cells, Art. Org.*, vol. 16, No. 4, pp. 815–828 (1988).

Lin, Shan–Yang, et al., "Microencapsulation and controlled release of insulin from polylactic acid microcapsules", *Biomat. Med. Dev., Art. Org.*, vol. 13, Nos. 3&4, pp. 187–201 (1985–86).

Mathiowitz, E., et al., "Polyanhydride Microspheres as Drug Carriers. II. Microencapsulation by Solvent Removal", *Journal of Applied Polymer Science*, vol. 35, pp. 755–774 (1988).

Splenlehauer, G., et al., "In vitro and in vivo degradation of poly(D,L lactide/glycolide) type microspheres made by solvent evaporation method", *Biomaterials*, vol. 10, pp. 557–563 (Oct. 1989).

Thies, Curt, "Microcapsules as Drug Devices Systems", *Crit. Rev. Biomed. Eng.*, vol. 8, Issue 4, pp. 335–383 (1982).

Windholz M., et al. *The Merck Index*, 10th Edition, p. 37, Abstract # 225 (1983).

Thomas R. Tice, et al. Biodegradation of Microcapsules and Biomedical Devices Prepared with Resorbable Polyesters, Southern Research Institute, University of Alabama. (pp. 21–23).

William T. Buchanan, et al. Systemic Effects of epinephrine–impregnated retraction cord in fixed partial denture prosthodontics, JADA, vol. 104, Apr. 1982.

David B. Masters, et al., Sustained Local Anesthetic Release from Bioerodible Polymer Matrices: A Potential Method for Prolonged Regional Anesthesia, Pharmaceutical Research, vol. 10, No. 10, pp. 1527–32,1993.

N.H. Shah, et al., A biodegradable injectable implant for delivering micro and macromolecules using poly (lactic–co–glycolic) acid (PLGA) copolymers, Journal of Controlled Release, 27 (1993) 139–147.

D.L. Williams, Microencapsulated Local Anesthetics, Proc. Int Symp. Rel Bioact Mater, 11:69–070 (1984).

Journal of Dental Research, IADR Abstract Papers, vol. 61, Papers 860 and 861, Mar. 1982.

Richard L. Dunn, et al., Monolithic Fibers for Controlled Delivery of Tetracycline, Southern Research Institute (pp. 157–159).

Thomas R. Tice, Controlled Release of Ampicillin and Gentamicin from Biodegradable Microcapsules, Southern Research Institute.

Roland Bodmeier, et al., Polylactic microspheres containing quinidine base and quinidine sulphate prepared by the solvent evaporation method. III. Morphology of the microspheres during dissolution studies, J. Microencapsulation, vol. 5, No. 4, pp. 323–330, 1988.

Marshall Devor, et al., Corticosteroids Suppress Ectopic Neural Discharge Originating in Experimental Neuromas, Pain, 22 pp. 127–137, (1985).

G. McCleane, M.D., et al., The addition of triamcinolone acetonide to bupivacaine has no effect on the quality of analgesia produced by ilioinguinal nerve block, Anaesthesia, vol. 49, pp. 819–820, 1994.

Naoki Wakiyama, et al., Influence of physiochemical properties of polylactic acid on the characteristics and in vitro release patterns of polylactic acid microspheres containing local anesthetics, Chem. Pharm. Bull, 30 (7), pp. 2621–2628, !982.

Duncan H. Haynes, Ph.D., et al., Ultra–long–duration Local Anesthesia Produced by Injection Lecithin–coated Methoxyflurane Microdroplets, Anesthesiology, 63:490–499, 1985.

Berde, C.B., et al., "Sustained Release of Dibucaine from a Biodegradable Polymer Matrix: A Potential Method for Prolonged Neural Blockade", Abstracts of Scientific Papers, 1990 Annual Meeting, Amer. Soc. Anesthesiologists, 73:A776 (Sep. 1990).

Edelman, Elazer R., et al., "Optimization of release from magnetically controlled polymeric drug release devices", Biomaterials, 14(8):621–626 (1993).

Masters, et al., Abstract No. 94.3, "Prolonged Sciatic Nerve Blockade Using Sustained Release of Veratridine From a Biodegradable Polymer Matrix", Soc. Neurosci. Abstr., 18:200 (1992).

Fong, Jones W., et al., "Evaluation of biodegradable microspheres prepared by a solvent evaporation process using sodium oleate as emulsifier", Journal of Controlled Release, 3:119–130 (1986).

Fong, J.W., "Microencapsulation by Solvent Evaporation and Organic Phase Separation Processes," pp. 81–108, chapter 5 from Controlled Release Systems: Fabrication Technology, Ed. Dean Hsieh, Ph.D., vol. 1 (1988).

Masters, David B., et al.,"Prolonged Regional Nerve Blockade by Controlled Release of Local Anesthesia from a Biodegradable Polymer Matrix", Anesthesiology, 79:340–346 (1993).

Miyazaki, S., et al., "External control of drug release: controlled release of insulin from a hydrophilic polymer implant by ultrasound irradiation in diabetic rats", J. Pharm. Pharmacol., 40:716–717 (1988).

Sato, T., et al., "Porous Biodegradable Microspheres for Controlled Drug Delivery. I. Assessment of Processing Conditions and Solvent Removal Techniques", Pharmaceutical Research, 5:21–30 (1988).

Schneider, Markus, M.D., et al., "A Preferential Inhibition of Impulses in C–fibers of the Rabbit Vagus Nerve by Veratridine, an Activator of Sodium Channels", Anesthesiology, 74:270–280 (1991).

Tice, Thomas R., et al., "Preparation of Injectable Controlled–Release Microcapsules by a Solvent–Evaporation Process", Journal of Controlled Release, 2:343–352 (1985).

Wakiyama, Naoki, et al., "Preparation and Evaluation in Vitro and in Vivo of Polylactic Acid Microspheres containing Dibucaine", Chem. Pharm. Bull, 30:3719–3727 (1982).

Abstract: Li, J. et al., "Analgesic Dilator for Use in Cervican and Uterine Operations," XP–002144657, CN1091041 A.

Duncan, et al., "Treatment of Upper Extremity Reflex Sympathetic Dystrophy with Joint Stiffness Using Sympatholytic Bier Blocks and Manipulation" Orthopedics 11(6), pp. 883–886, (1988).

Flanagan, et al., "Intra–articular injection for pain relief in patients awaiting hip replacement", Ann. Royal Coll. Surg. Eng., vol. 70, pp. 156–157 (1988).

Glasser, et al., "The perioperative use of corticosteroids and bupivacaine in the management of lumbar disc disease", J. Neurosurg., vol. 78, pp. 383–387, (1993).

Guttu, et al., "Delayed Healing of Muscle After Injection of Bupivacaine and Steroid", Annals of Dentistry, 49:5–8, (1990).

Hall, et al., "Acute effects of intravenous glucocorticoid on cat spinal motor neuron electrical properties", Brain Research, vol. 240, pp. 186–190, (1982).

Sandrock and Warfield, "Epidural Steroids and Facet Injections", Ch. 29 Principles and Practice of Pain Management, Warfield, C.A., editor (McGraw–Hill, Inc. 1993).

Waldman, et al., "The Relief of Body Wall Pain Secondary to Malignant Hepatic Metastases by Intercostal Nerve Block with Bupivacaine and Methylprednisolone", J. Pain Symptom Management, 3(1), 39–43 (1988), (see in particular p. 42, column 2).

Bonica, John J. and F. Peter Buckley, "Regional Analgesiawith Local Anesthetics", The Management of Pain II; pp. 1883–1966, (1990), Lea & Febiger (Eds.) Second Edition.

Lewis, D.H., et al., "The Use of In Vitro Release Methods to Guide the Development of Controlled–Release Formulations", 9th International Symposium on Controlled Release of Bioactive Maerials, Sponsored by Controlled Release Society, Inc., pp. 61–64.

Masters, D.B., et al., Meeting for the American Society of Anesthesiologists, vol. 75:A680, (1991).

Devor, et al., 1983, "Axoplasmic Transport Block Reduces Ectopic Impulse Generation in Injured Peripheral Nerves", pp. 73–85.

Schnebel, et al., "The Use of Oral Colchicine for Low–Back Pain", 1987, pp. 354–357.

March, et al., "Biodegradable Microspheres Containing a Colchicine Analogue Inhibit DNA Synthesis in Vascular Smooth Muscle Cells", 1994, pp. 1929–1933.

CA 125:104914, , Joanne Curley, et al., "Prolonged regional nerve blockade: Injectable biodegradable bupivacaine/polyester microspheres".

Jean–Marc Malinovsky, et al., "Motor and Blood Pressures Effects of Epidural Sustained–Release Bupivacaine from Polymer Microspheres: A Dose–Response Study in Rabbits", Anesth Analg 1995, 81:519–24.

L.S. Goodman, et al., "The Pharmacological Basis of Therapeutics", Fourth Edition, 1970, The MacMillan Co., p. 372.

Vol. IA "Drug Information for the Health Care Professional", USP DI, 1989, Ninth Edition, Anesthetics (Mucosal–Local), pp. 183–184; 196–197; 201–203.

Setterstrom, Tice, Lewis and Meyers, "Controlled Release of Antibiotics from Biodegradable Microcapsules fro Wound Infection Control", U.S. Army Institute of Dental Research, (1982), 12 pages.

Abstract: Archer DR, et al. "Changes in slow axonal transport of tubulin induced by local application of colchicine to rabbit vagus nerve", Acta Physiol Scand 1994 Jan. 150(1):57–65.

Abstract: Lim, J.–O., et al., "Prolonged Sciatic Nerve Blockade II: Local Anesthetic–Polymer Microspheres," Anesthesiology vol. 83, pp. A810 (1995).

Abstract: Le Corre, et al., "Spinal controlled delivery of bupivacaine from DL–lactic acid oligomer microspheres", J. Pharm Sci 1995 Jan. 84(1) 75–78.

Abstract: Gradus–Pizlo, et al., "Local delivery of biodegradable microparticles containing colchicine or a . . . ", J.Am.Coll. Cardiol. 1995 Nov. 26(6) 1549–57.

Abstract: Penickova V., et al., "Vinblastin iontophoresis in treating intractable pain", Acta Univ Palacki Olomuc Fac Med 1990 128:37–47.

Abstract: Kantner, et al., Regulatory mechanisms for substance P in the dorsal horn during a nociceptive stimulus: axoplasmic transport vs. electrical activity., Brain Res., Oct. 22, 1986 385(2):282–90.

Abstract: Yamamoto, et al., "Effects of colchicine applied to the colchicine applied . . . constriction", Pain, Nov. 1993, 55(2):227–33.

* cited by examiner

FORMULATIONS AND METHODS FOR PROVIDING PROLONGED LOCAL ANESTHESIA

This application is a continuation application of U.S. patent application Ser. No. 08/714,783, filed Sep. 16, 1996 now U.S. Pat. No. 6,046,187, the disclosure of which is herein incorporated by reference.

The U.S. Government may have rights in this invention pursuant to National Institutes of Health Grant No. GM-15904 to Harvard Anesthesia Research and Teaching Center to C. Berde, and Grant No. CA 5257 to R. Langer.

BACKGROUND OF THE INVENTION

This invention is generally in the field of anesthesiology and, in particular, the restoration and/or boosting of a previously administered local anesthesia by the use. of a non-local anesthetic agent to reactivate and/or prolong local anesthesia.

Methods and/or formulations heretofore used to provided localized anesthesia are advantageously reversible so that nerve conduction and motor and/or sensory function returns. However, in many situations it becomes necessary to repeat the same local anesthesia one or more additional times in order to protect a patient from chronic pain or from pain induced by repeated surgical or medical procedures.

In order to provide local and/or anesthesia for extended periods, clinicians currently use local anesthetic agents administered through a catheter or syringe to a site where anesthesia is to be induced. Thus, prolonged local anesthesia, over a period of greater than about 6 hours, has heretofore required that local anesthetic be administered either as a bolus or through an indwelling catheter connected to an infusion pump. Similarly, heretofore, reactivation of local anesthesia has required repeated administered of a local anesthetic through an indwelling catheter or by reinjection. These methods have the disadvantage of potentially causing irreversible damage to nerves or surrounding tissues due to fluctuations in local anesthetic concentration and in the accumulation and diffusion of potentially toxic levels of local anesthetic into the systemic circulation.

One approach to this problem is to provide for a prolonged, sustained local anesthesia, as is disclosed by WO 94/05265. This published international patent application describes improved biocompatible controlled release systems consisting of a polymeric matrix incorporation of a local anesthetic for the prolonged administration of the local anesthetic agent. The devices are selected on the basis of their degradation profiles: release of the local anesthetic in a linear, controlled manner over the period of preferably two weeks and degradation in vivo with a half-life ranging from less than six months to about a year and more, and preferably from about two to four weeks, to induce localized anesthesia. The anti-inflammatories that are said to be useful include steroids such as dexamethasone, cortisone, prednisone, and others routinely administered orally or by injection. The exemplified pellet formulations comprise only about 20% local anesthetic and this published international patent application teaches that the selection of the polymers is critical to providing a sustained release of the local anesthetic agent. This publication also teaches that the anti-inflammatory agent serves to prevent localized tissue inflammation and encapsulation of the injection site with a connective tissue capsule. However, the local anesthesia so provided is of necessity prolonged, without any option for modulating the level of anesthesia.

Local anesthetic agents have been incorporated into biocompatible polymeric devices, such as, for example, polylactic acid microspheres, as described by Wakiyama, et al., Chem. Pharm. Bull., 30:3719–3727 (1982). In contrast to the lipid based materials, the poly(lactic acid) devices take over a year to degrade and cause localized inflammation. Berde, et al., Abstracts of Scientific Papers, 1990 Annual Meeting, Amer. Soc. Anesthesiologists, 73:A776 (September 1990), reported the use of a device formed of a polyanhydride polymer matrix of copolymer 1,3 bis(p-carboxyphenoxy)propane and sebacic acid, in a ratio of 1:4, into which dibucaine free base was incorporated by compression molding. This drug-polymer device, however, had several drawbacks. For example, because the drug was incorporated into the polymer matrix by compression molding, the device sometimes displayed bulk erosion, causing fast initial release of drug.

Nevertheless, heretofore there has been no method or formulations known to the art for reactivating, prolonging or otherwise boosting a previously administered local anesthesia without the use of repeated dose of a local anesthetic.

Accordingly, it is an object of the present invention to provide methods and compositions for modulating local anesthesia by administering one or more glucocorticosteroid agents (also referred to herein as glucocorticoid agents) before, simultaneously with or after the administration of a local anesthetic at a site in a patient. It is a further object of the present invention to provide methods and compositions that are able to reactivate or prolong local anesthetic activity that has previously diminished or worn off It is a still further object of the present invention to provide methods and compositions for modulating the degree of local anesthesia wherein the active restorative or prolonging agents are pharmaceutically acceptable glucocorticosteroids that are locally or systemically administered to a patient needing or desiring to restore a previously induced local anesthesia.

SUMMARY OF THE INVENTION

In accordance with the above-mentioned objects and others, the invention is related to methods and compositions for reactivating and/or prolonging a local anesthetic effect, that has previously been induced by an implanted or injected local anesthetic formulation.

Accordingly, the present invention broadly provides methods for reactivating and/or prolonging an induced local anesthesia at a site in a patient in need thereof, comprising administering to the patient at a site at which local anesthesia was previously induced, a pharmaceutically acceptable composition that includes a glucocorticosteroid in an amount effective to reactivate and/or prolong the previously induced local anesthesia. The previous local anesthesia is induced by any art known local anesthetic or by a combination of any suitable art-known local anesthetic and any suitable art-known glucocorticosteroid.

The glucocorticosteroid for reactivating and/or prolonging a local anesthesia is administered by, e.g., systemic administration, e.g., orally or intravenously, or by implantation, infiltration, injection and/or infusion at or adjacent to the site requiring reactivated or prolonged anesthesia, and is administered, for example, before or after the local anesthesia has substantially worn off, to provide reactivation and/or prolongation of the effect. At least a portion of the glucocorticoid is administered, simply by way of example, at a time ranging from about 1 to about 72 hours or more, from about 1 to about 36 hours, from about 1 to about 24 hours, from about 1 to about 12 hours, from about 1 to about 6 hours, and from about 1 to about 4 hours, or from about 4 to about 72 hours and from about 4 to about 24 hours, after the time that the (e.g., first) local anesthetic was administered.

The previously administered local anesthetic is, for example, bupivacaine, ropivacaine, dibucaine, procaine, chloroprocaine, prilocaine, mepivacaine, etidocaine, tetracaine, lidocaine, xylocaine, and salts thereof or any other pharmaceutically acceptable art-known local anesthetic or mixtures thereof. The glucocorticosteroid is, e.g., dexamethasone, cortisone, prednisone, hydrocortisone, beclomethasone dipropionate, betamethasone, flunisolide, methylprednisone, paramethasone, prednisolone, triamcinolone, alclometasone, amcinonide, clobetasol, fludrocortisone, diflorasone diacetate, fluocinolone acetonide, fluocinonide, fluorometholone, flurandrenolide, halcinonide, medrysone and mometasone and pharmaceutically acceptable mixtures thereof and salts thereof or any other suitable art-known glucocorticosteroid, either naturally occurring or synthetic.

In the method according to the invention, at least a portion of the glucocorticosteroid may be administered systemically, e.g., orally or by systenmic injection, but is preferably administered locally at the desired site in a patient. The locally administered glucocorticosteroid can be administered in immediate release form, in controlled release form or in both immediate release and controlled release form. The immediate release and/or controlled release forms are preferably prepared in a form suitable for injection, infusion and/or application in a pharmaceutically acceptable medium, e.g., as a solution, suspension or even, e.g., as a plurality of microspheres incorporating one or more agents, including a glucocorticosteroid. When controlled release microspheres are provided, at least a portion of the glucocorticosteroid is optionally in immediate release form in the injection medium.

The methods according to the present invention provide a local anesthesia prolonged by reactivation of a previously administered local anesthetic agent, the reactivation providing a local anesthesia having a duration ranging from, e.g., about 1.1 to about 14 fold, or more, of the duration of local anesthesia induced by controlled release local anesthetic without glucocorticosteroid enhancement. In a preferred embodiment, the methods, the prolongation ranges from about 6 to about 13 fold of the duration of local anesthesia induced by controlled release local anesthetic without glucocorticosteroid enhancement. The methods according to the invention are therefore capable of providing an initial period of local anesthetic induced anesthesia, that is either prolonged or that is reactivated to provide a local anesthesia with a duration ranging from about 1 to about 72 hours or more, from about 1 to about 36 hours, from about 1 to about 24 hours, from about 4 to about 8 hours and from about 1 to about 2 hours, measured from the time of administration of the reactivating composition.

Further, the invention also provides pharmaceutical formulations for providing a regional local anesthesia in a patient that, when administered to a local site in a patient, sequentially releases an effective amount of a pharmaceutically acceptable local anesthetic and then at a time after administration, releases an amount of a glucocorticosteroid effective to reactivate and/or prolong the local anesthesia. Such a pharmaceutical formulation according to the invention also includes an effective amount of a biocompatible, controlled release material effective to prolong the release of said local anesthetic from said formulation and effective to delay the release of the glucocorticosteroid for a desired time after administration. Simply by way of example, the glucocorticoid agent according to the invention can be released or administered at the desired site at any time, but preferably at least a portion that is effective to prolong and/or reactivate the desired local anesthesia is released or administered after the local anesthetic has been administered. At least a portion of the glucocorticoid is released from said formulation, simply by way of example, at a time ranging from about 1 to about 72 hours or more, from about 1 to about 36 hours, from about 1 to about 24 hours, from about 1 to about 6 hours, or from about 4 to about 24 hours and from about 1 to about 2 hours, measured from the time that the (e.g., first) local anesthetic was administered.

While any pharmaceutically acceptable controlled release material may be employed, the pharmaceutically acceptable controlled release materials preferably are prepared from a polymer such as, for example, polyanhydrides, copolymers of lactic acid and glycolic acid, poly(lactic) acid, poly (glycolic) acid, polyesters, polyorthoesters, proteins and/or polysaccharides.

A pharmaceutically acceptable local anesthetic is, for example, ropivacaine, bupivacaine, dibucaine, etidocaine, tetracaine, lidocaine, xylocaine, mixtures thereof, and salts thereof and others well known to the art. The local anesthetic is incorporated into the controlled release formula at a weight percent ranging from about 0.1 to about 90%

A pharmaceutically acceptable glucocorticosteroid. includes, e.g., dexamethasone, cortisone, prednisone, hydrocortisone, beclomethasone dipropionate, betamethasone, flunisolide, methylprednisone, paramethasone, prednisolone, triamcinolone, alclometasone, amcinonide, clobetasol, fludrocortisone, diflorasone diacetate, fluocinolone acetonide, fluocinonide, fluorometholone, flurandrenolide, halcinonide, medrysone and/or mometasone and pharmaceutically acceptable mixtures salts thereof or any other suitable glucocorticosteroid known to the art. Preferably, dexamethasone is used.

The pharmaceutically acceptable formulation according to the invention provides a reactivated local anesthesia of a duration ranging from about 1.1 to about 14 fold, or more, of the duration of local anesthesia induced by controlled release local anesthetic without glucocorticosteroid enhancement. In a preferred embodiment, the methods, the prolongation ranges from about 6 to about 13 fold of the duration of local anesthesia induced by controlled release local anesthetic without glucocorticosteroid enhancement. The methods and formulations according to the invention are therefore capable of providing an initial period of local anesthetic induced anesthesia, followed by a second period of anesthesia, that is either prolonged or that is reactivated to provide a second period of local anesthesia.

BRIEF DESCRIPTION OF THE DRAWINGS

The following drawings are illustrative of embodiments of the invention and are not meant to limit the scope of the invention as encompassed by the claims.

square), copolymer of lactic and glycolic acid ("PLGA") 65:35 (circle), and PLGA 75:25 (triangle) loaded with bupivacaine and dexamethasone, administered at doses of 50 to 450 mg of bupivacaine/Kg rat. Duration was defined as the mean duration of time for which the for which the latency of a group of 5 rats was greater than or equal to 7 seconds. Error bars indicate standard errors.

Figure 2:
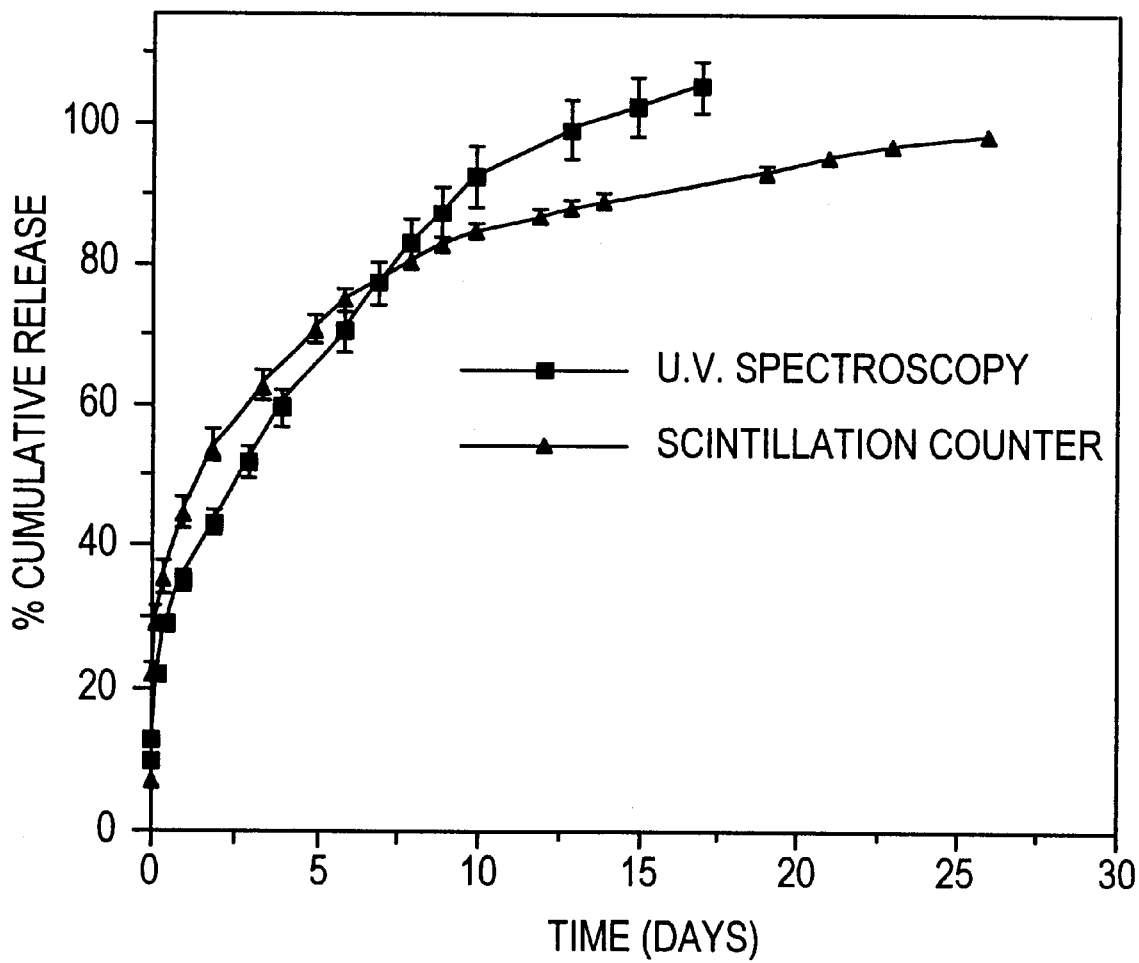

FIG. 2. Shows comparison of two methods, ultraviolet ("UV") spectroscopy and scintillation counting of isotope-labeled drug, confirming that both methods are essentially equivalent in tracing drug released from microspheres.

Figure 3A:
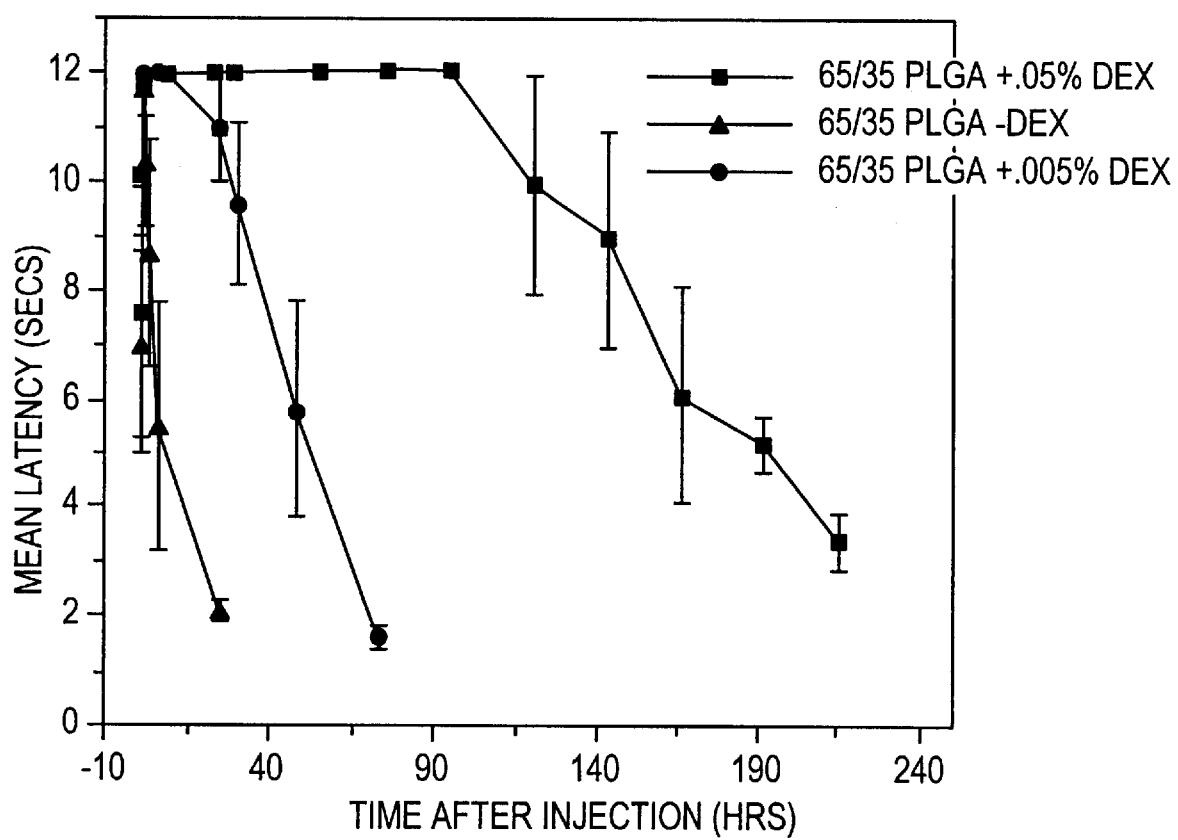

FIG. 3A. Duration of sensory latency, (secs) versus time after injection (hours), determined by the modified hot plate test for 75% bupivacaine loaded PLGA 65:35 containing 0.05% (closed square), 0.005%.(closed circles), and 0.0% (closed triangles) dexamethasone. Error bars indicate standard errors.

Figure 3B:
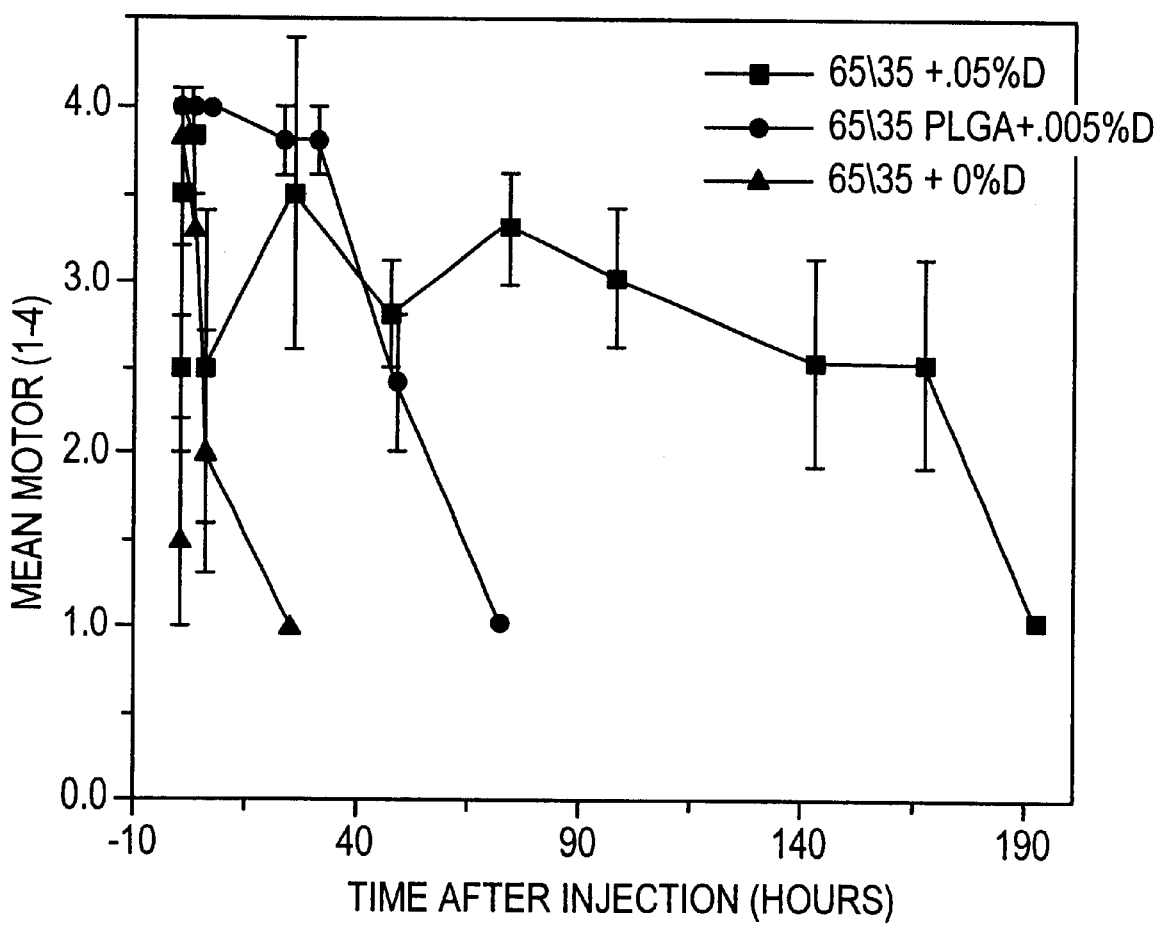

FIG. 3B. Duration of motor anesthesia in seconds ("secs") versus time after injection (hours), determined by motor function testing for 75% bupivacaine loaded PLGA 65:35 containing 0.05% (closed square), 0.005% (closed circles), and 0.0% (closed triangles) dexamethasone. Error bars indicate standard errors.

Figure 4A:
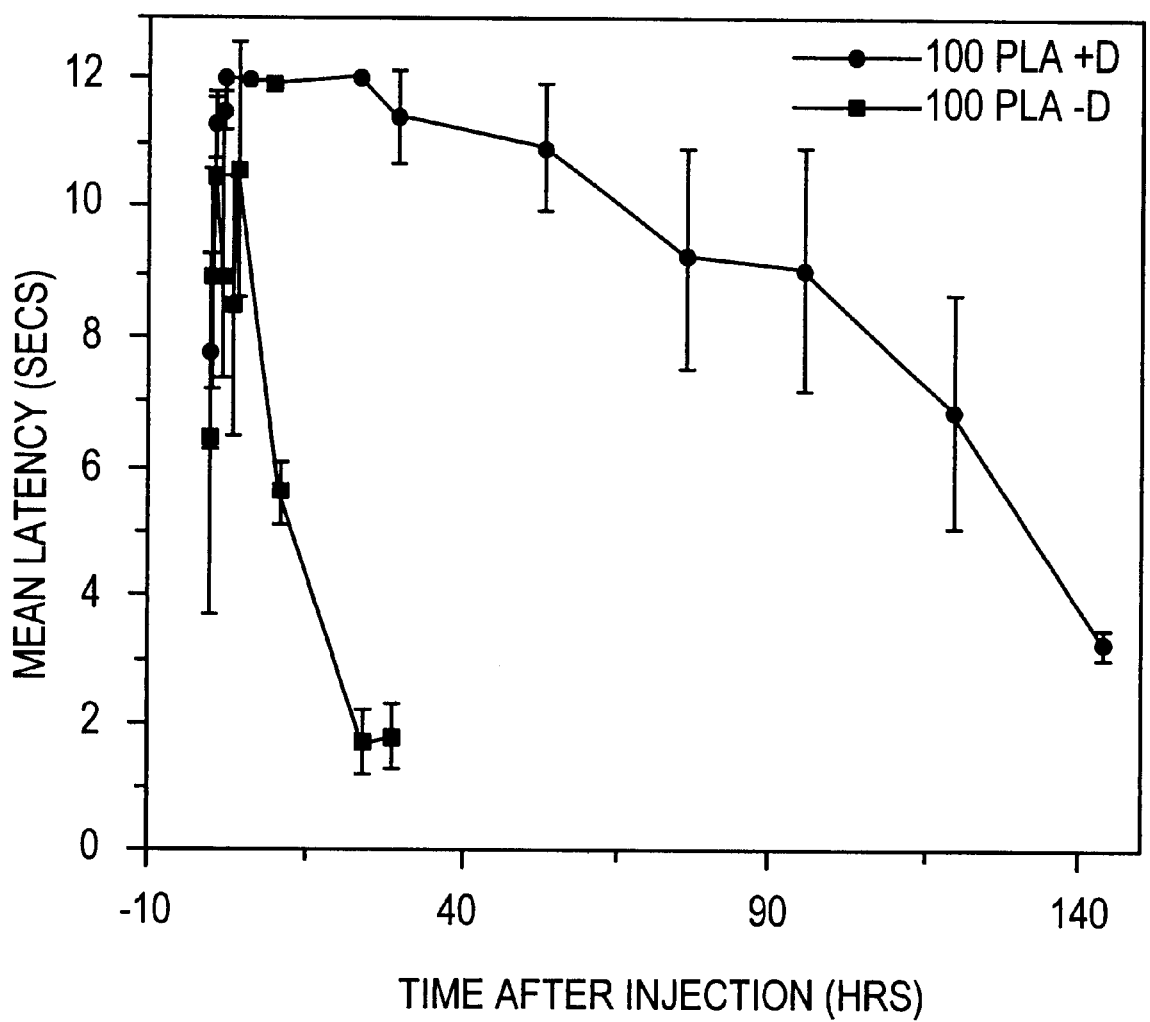

FIG. 4A. Duration of mean latency (secs) verses time after injection (hrs) for PLA 100 microspheres loaded with 75% bupivacaine which contained 0.05% dexamethasone (closed circles) with corresponding microspheres which did not contain dexamethasone (closed squares) administered at 150 mg of bupivacaine per kg of rat.

Figure 4B:
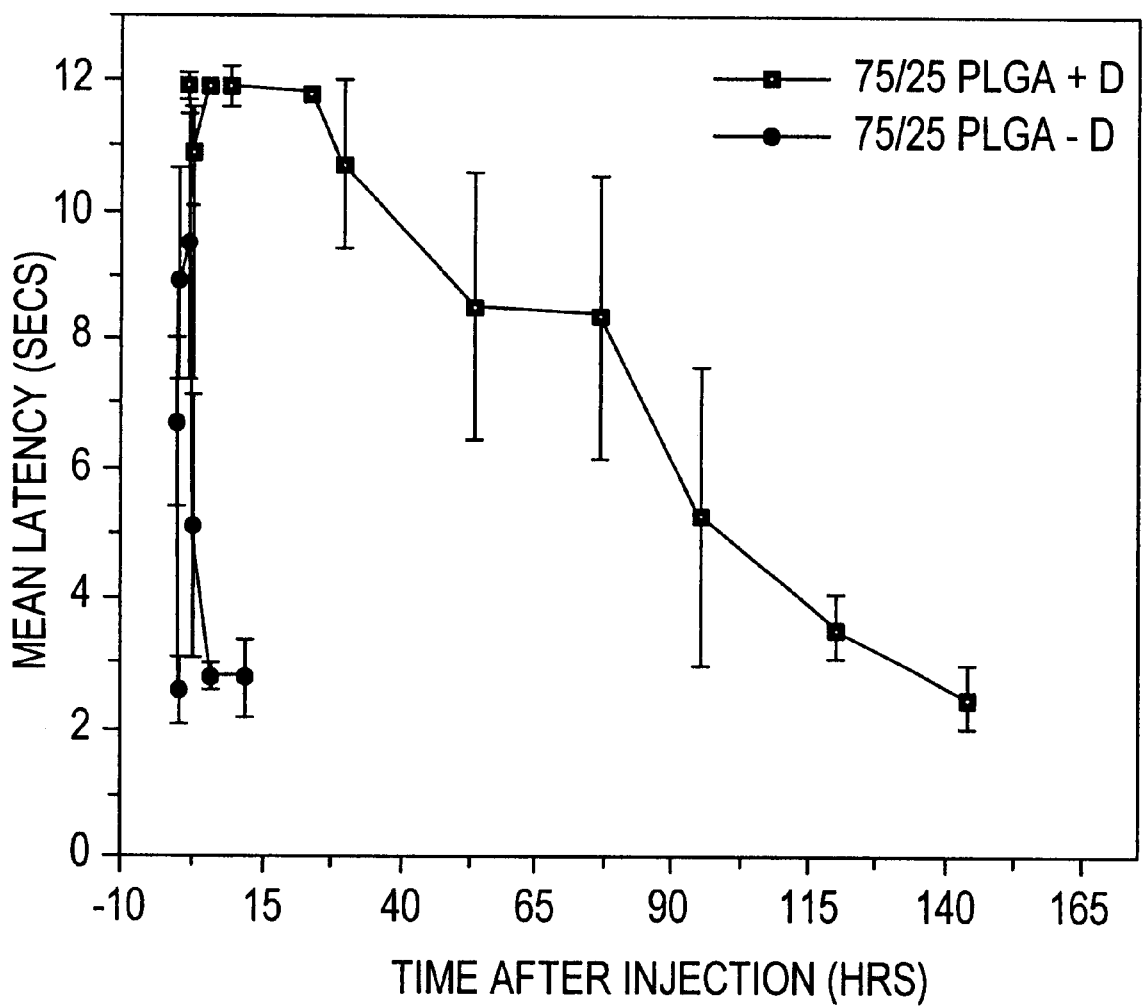

FIG. 4B. Duration of mean latency (secs) verses time after injection (hrs) for PLGA 75:25 microspheres loaded with 75% bupivacaine which contained 0.05% dexamethasone (closed squares) with corresponding microspheres which did not contain dexamethasone (closed circles) administered at 150 mg of bupivacaine per kg of rat.

Figure 4C:
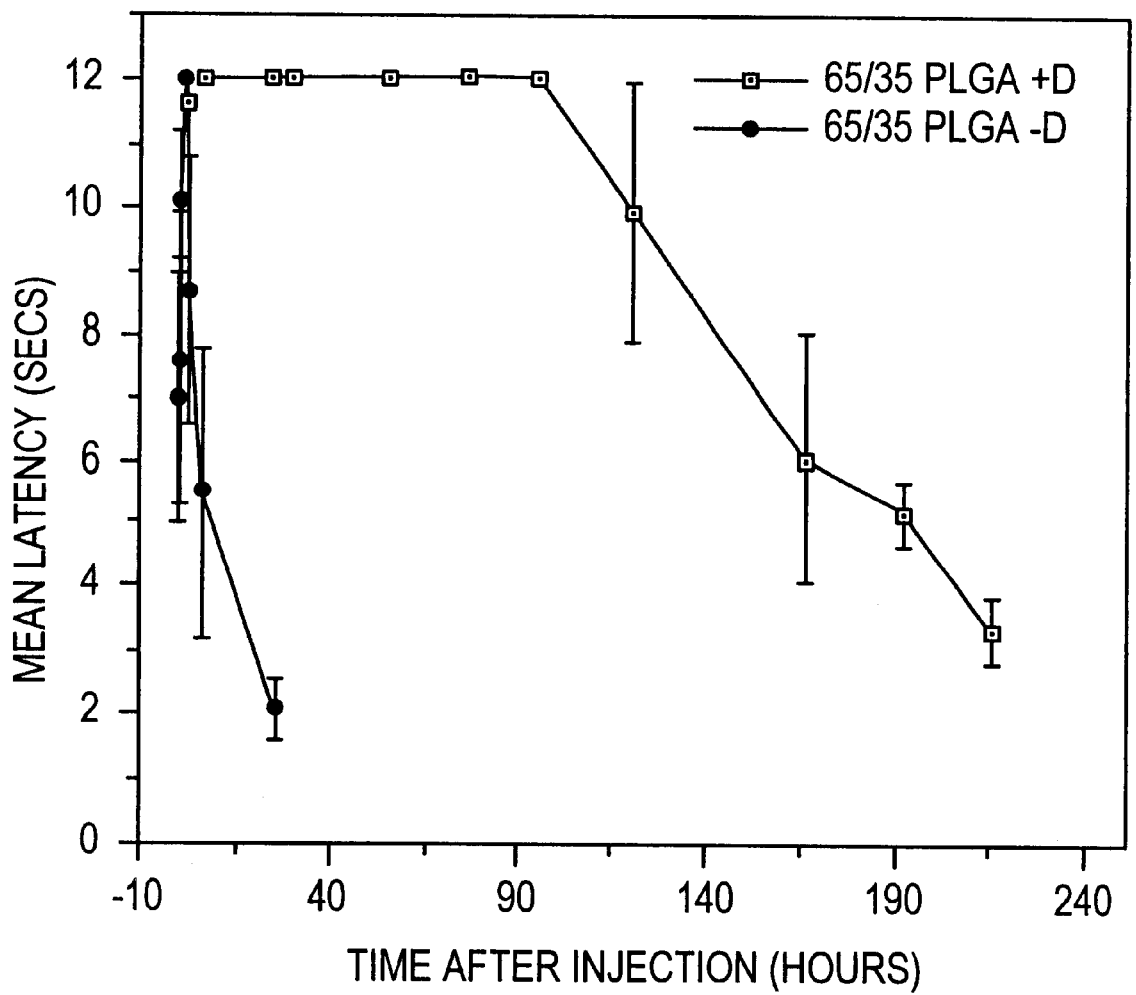

FIG. 4C. Duration of mean latency (secs) verses time after injection (hrs) for PLGA 65:35 microspheres loaded with 75% bupivacaine which contained 0.05% dexamethasone (open squares) with corresponding microspheres which do not contain dexanethasone (closed circles) administered at 150 mg of bupivacaine per kg of rat.

Figure 4D:
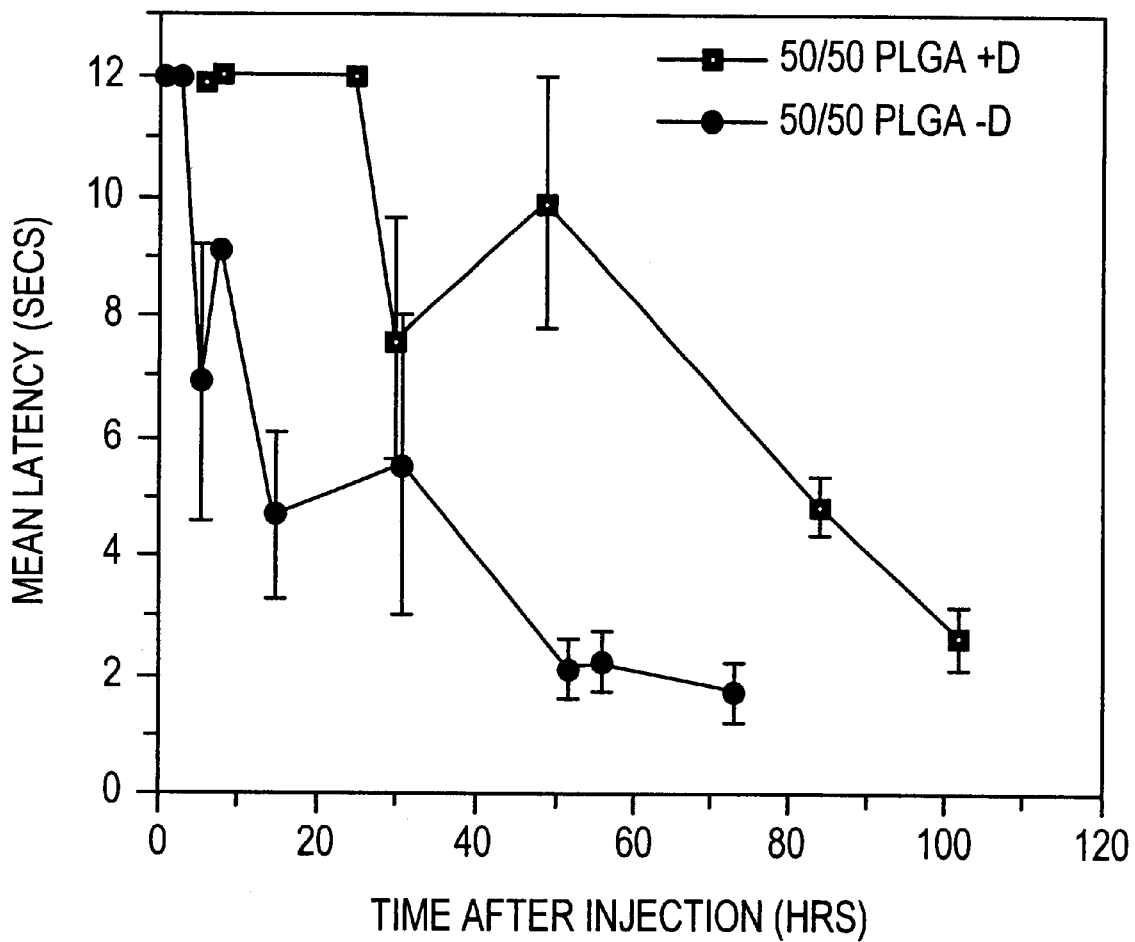

FIG. 4D. Duration of mean latency (secs) verses time after injection (hrs) for PLGA 50:50 microspheres loaded with 75% bupivacaine which contained 0.05% dexamethasone (closed squares) with corresponding microspheres which do not contain dexamethasone (closed circles) administered at 150 mg of bupivacaine per kg of rat. Error bar indicate standard errors.

Figure 5A:
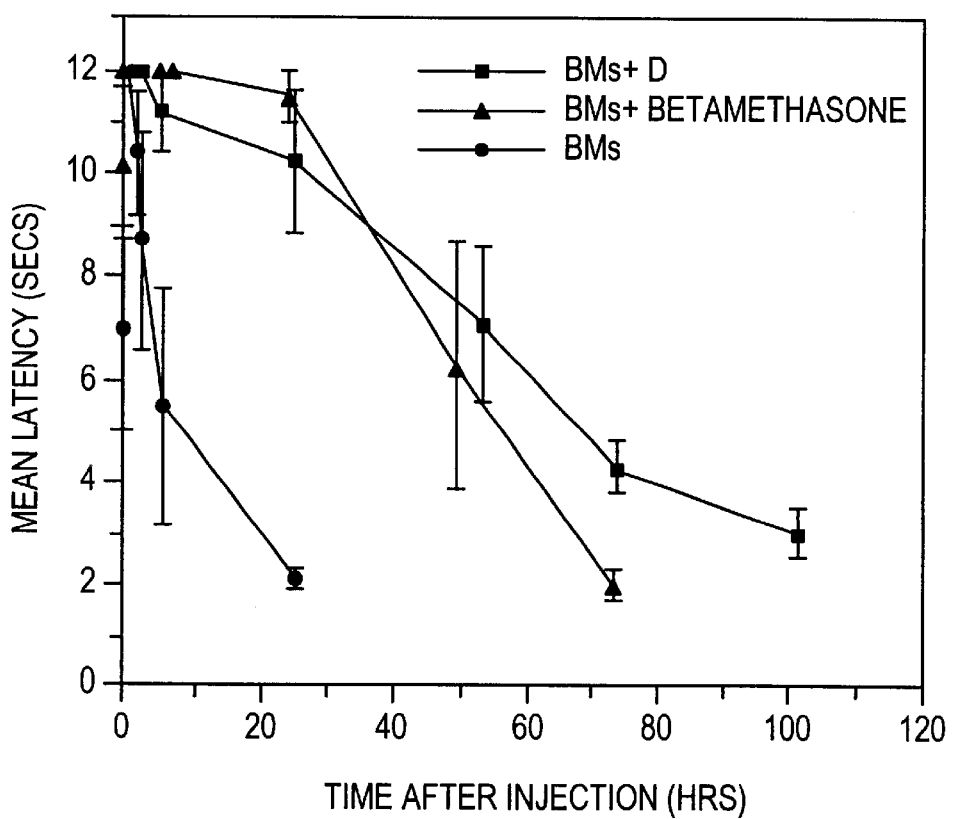

FIG. 5A. Duration of mean latency (secs) verses time after injection (hrs) for bupivacaine-loaded microspheres with dexamethasone in the injection fluid (closed squares), bupivacaine-loaded microspheres with betamethasone (closed triangles) in the injection fluid and control microspheres with bupivacaine only (closed circles) (Ms= microspheres).

Figure 5B:
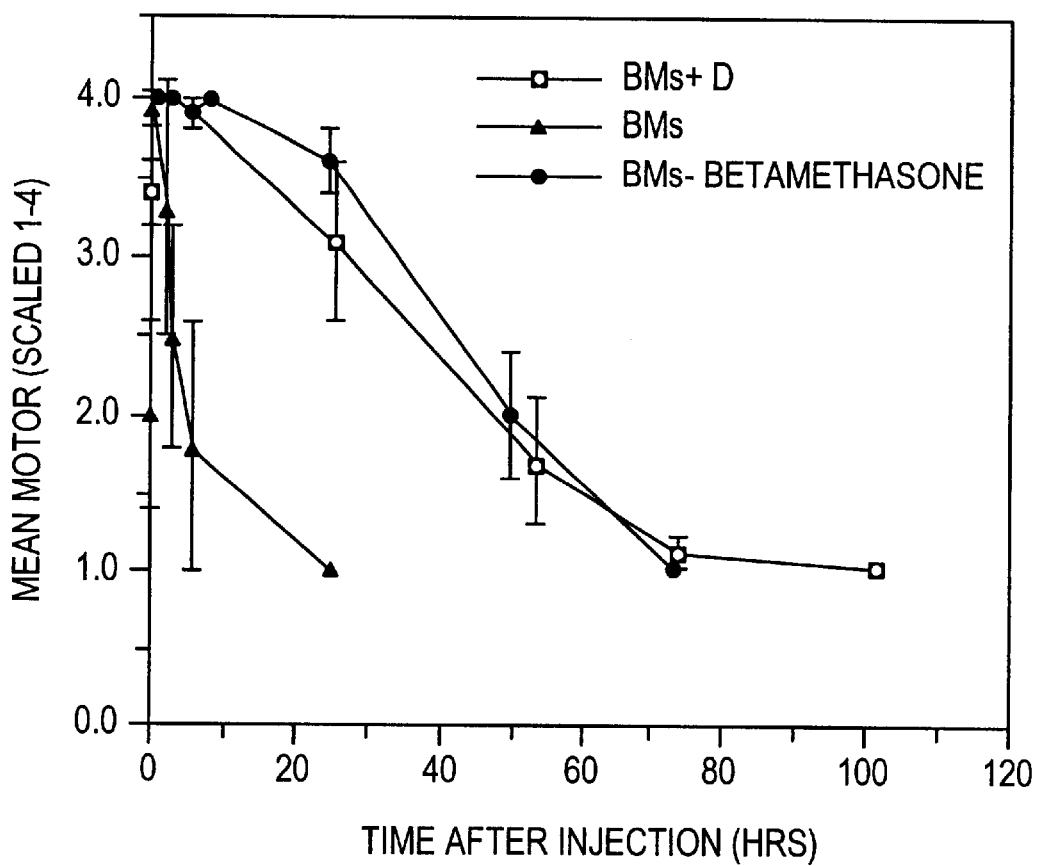

FIG. 5B. Graph of mean motor anesthesia (scaled 1–4) verses time (hrs) for bupivacaine-loaded microspheres with dexamethasone in the injection fluid (open squares) and bupivacaine-loaded microspheres with betamethasone in the injection fluid (closed triangles) and control microspheres with bupivacaine only (closed circles).

Figure 5C:
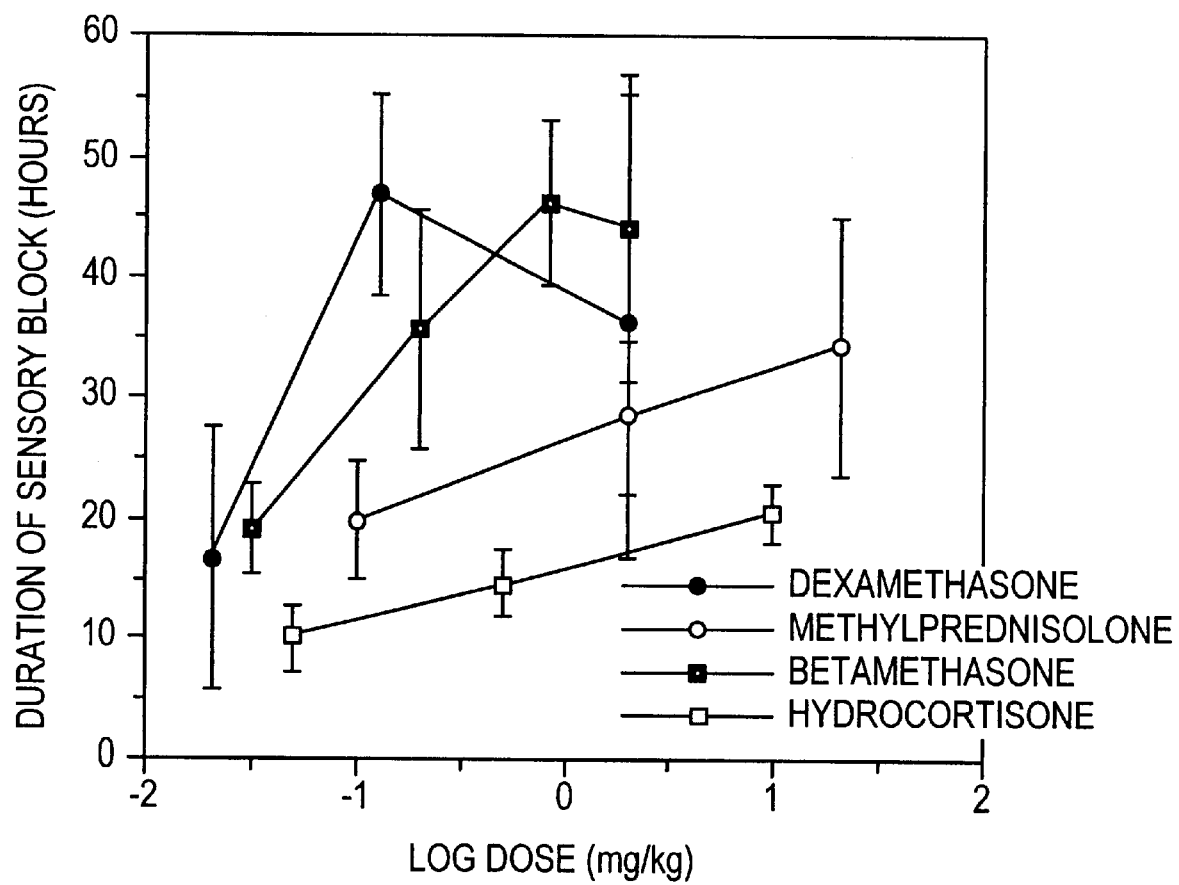

FIG. 5C. Graph of the duration of sensory block [y-axis; time (hours) from injection to a mean of hotplate latency of 7 seconds] verses log dose [x-axis; mg/kg] for various additives placed in the injection medium: bupivacaine microspheres plus dexamethasone (closed circles), methylprednisolone (open circles), betamethasone (closed squares) and hydrocortisone (open squares), (n=4–8 for each point).

Figure 6:
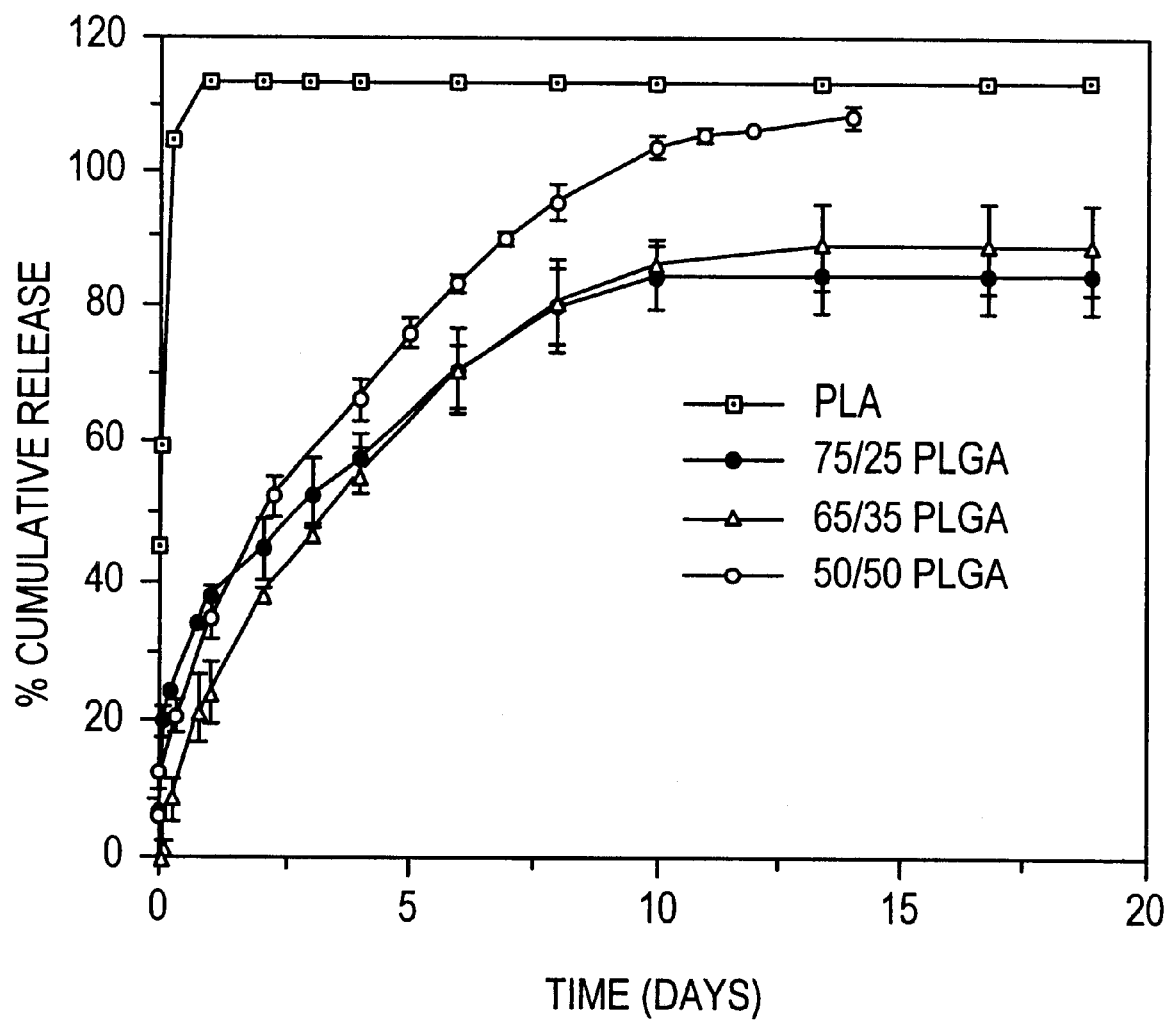

FIG. 6. Percent in vitro cumulative release versus time (days) for PLA 100 (square), PLGA 75:25 (closed circle), PLGA 65:35 (open triangle) and PLGA 59:50 (circle) microspheres loaded with 75% bupivacaine. Error bars indicate standard errors.

Figure 7:
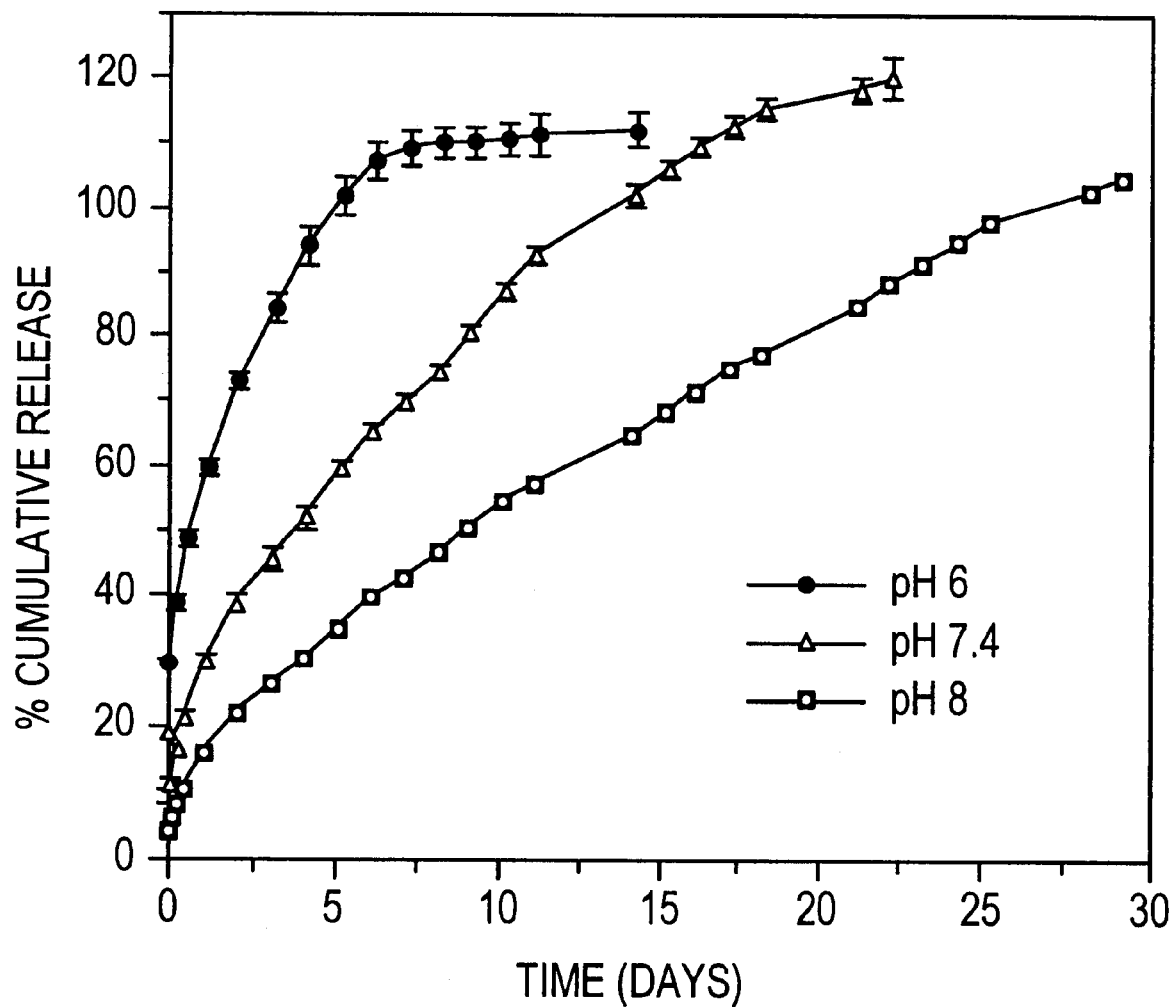

FIG. 7 shows. the percent cumulative release versus time (days) for PLGA, 175:25 microspheres loaded with about 75% bupivacaine in media at pH 6 (circles), pH 7.4 (triangles) and pH 8 (squares), respectively. Error bars indicate standard errors (n=4).

Figure 8A:
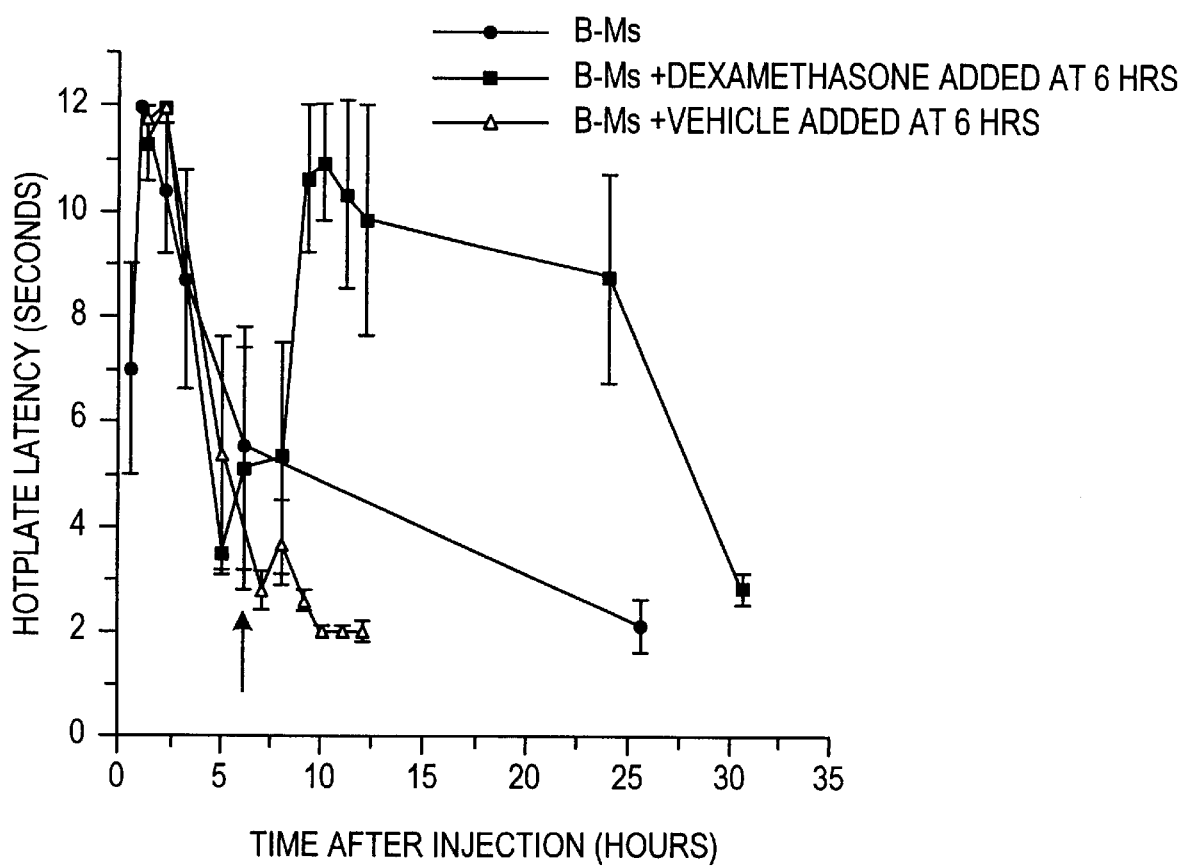

FIG. 8A shows sensory anesthesia as latency (secs) verses time after injection (hours) as induced by microspheres, PLGA 65:35, loaded with bupivacaine (about 75% percent loading, about 150 mg/kg) administered at zero hours followed by injection with dexamethasone at 6 hours: bupivacaine microspheres (circles), dexamethasone, 0.5 mg/kg, added at 6 hours (squares) and control vehicle added at 6 hours (triangles).

Figure 8B:
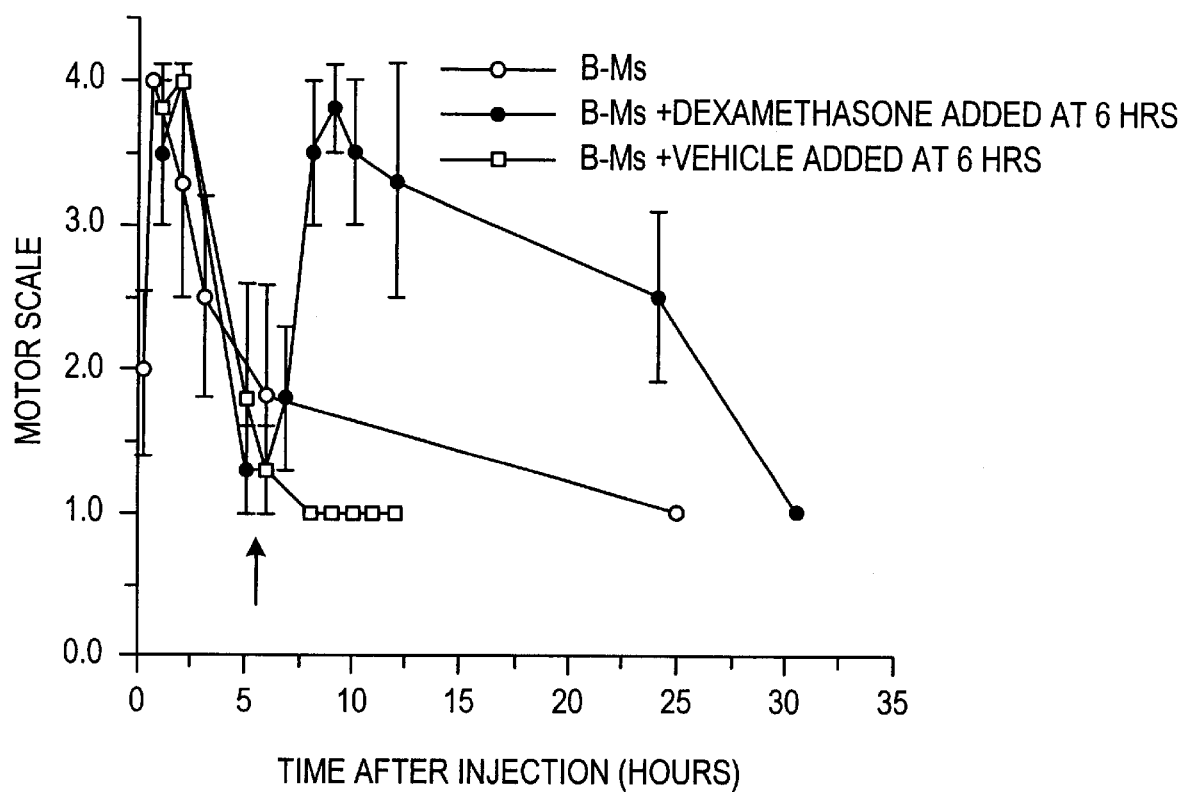

FIG. 8B. Motor anesthesia scale verses time (hrs) as induced by microspheres, PLGA 65:35, loaded with bupivacaine (about 75% percent loading, about 150 mg/kg) administered at zero hours followed by injection with dexamethasone 0.5% (closed circles) at 6 hours: bupivacaine microspheres (open circles), dexamethasone, 0.5 mg/kg, added at 6 hours (closed circles) and control vehicle added at 6 hours (open squares).

DETAILED DESCRIPTION OF THE INVENTION

Methods and compositions for modulating a local anesthesia, by the administration of an effective amount of at least one glucocorticosteroid agent, are provided. These methods and compositions can be used for the management of various forms of persistent or repetitive pain, such as postoperative pain, sympathetically maintained pain, or certain forms of chronic pain such as the pain associated with many types of cancer. The modulation according to the present invention can include restoring or reactivating a previous anesthesia that has waned and can also include restoring or reactivating a previous local anesthesia that has been induced by the previous co-administration of a local anesthetic and glucocorticosteroid agent.

As used herein, the term "patient" broadly refers to any animal that is to be treated with the compositions and by the methods herein disclosed. The disclosed local anesthetic dosage form, compositions and methods for restoring local anesthesia, can provide localized numbness and/or analgesia to any animal, e.g., any vertebrate, which it is desired to so anesthetize. In particular, the disclosed it methods and compositions will find use in veterinary practice and animal husbandry for, e.g., birds and mammals, wherever prolonged local anesthesia is convenient or desirable. In a preferred embodiment, the term includes a human or humans in need of or desiring reactivated local anesthesia.

In another aspect of the invention, a pharmaceutically effective glucocorticosteroid is administered locally or systemically, to a patient, before any local anesthetic is administered to the patient. In this aspect, the glucocorticosteroid dose will then potentiate, e.g., prolong the duration or increase the degree of local anesthesia of a later-administered local anesthetic.

As used herein, the term "local anesthetic agent" means any drug or mixture of drugs that provides local numbness and/or analgesia. Examples of local anesthetic agents which can be used include bupivacaine, ropivacaine, dibucaine, procaine, chloroprocaine, prilocaine, mepivacaine, etidocaine, tetracaine, lidocaine, and xylocaine, and mixtures thereof and any other art-known pharmaceutically acceptable local anesthetic. The local anesthetic can be in the form of a salt, for example, the hydrochloride, bromide, acetate, citrate, carbonate or sulfate. More preferably, the local anesthetic agent is in the form of a free base. Preferred local anesthetic agents include, e.g., bupivacaine. For bupivacaine, the free base provides a slower initial release and avoids an early "dumping" of the local anesthetic at the injection site. Other local anesthetics may act differently. Local anesthetic agents typically administered systematically may also be used in those cases where the means of administration results only in a local effect, rather than systemic.

The term "local anesthetic" may also encompass, pursuant to the definitions provided herein, a drug of a different class than those traditionally associated with local anesthetic properties, including but not limited to morphine, fentanyl, and agents which, for example, can provide anesthesia of nociceptive pathways (afferent and/or efferent). The formulations according to the invention preferably provide high load formulations of controlled release local anesthetic agent.

The term, "local anesthesia" includes the condition of e.g., a local numbness and/or analgesia, and/or inhibitory effects on sensory and motor function, induced, simply by way of example, by a local anesthetic as defined above.

The term, "controlled release" generally refers to compositions, e.g., pharmaceutically acceptable carriers, for controlling the release of an active agent or drug incorporated therein, typically by slowing the release of the active agent or drug in order to prevent immediate release. Such controlled release compositions and/or carriers are used herein to prolong or sustain the release of an active agent or drug incorporated, e.g., a local anesthetic and/or a glucocorticoid agent. Thus, the terms "controlled release" and "sustained release" are generally used interchangeably throughout this document unless otherwise indicated.

As used herein, the term "reactivate" refers to a process of prolonging the duration of an existing local anesthetic effect or of restoring a previously induced local anesthesia that is wearing off or that has fully worn off, by administering to a patient an effective amount of a glucocorticosteroid at a site that has previously been treated with a local anesthetic in that patient. Thus, after a certain amount of elapsed time, depending on the initial dose and rate of diffusion and/or release of a local anesthetic formulation, any local anesthetic effect, i.e., a local anesthesia, subsides or wears off, so that sensory or motor function is reactivated. If pain persists or recurs, the local anesthesia is optionally reactivated or prolonged before or after the local anesthesia begins to wear off.

According to the present invention, this is accomplished by delivering, e.g., topically applying inserting, infiltrating, injecting or even systemically administering, at least one pharmaceutically effective dose of a composition including a glucocorticosteroid agent at and/or adjacent to the site to be treated. Administration can also be by the automatic or controlled release of a glucocorticosteroid from a controlled release formulation previously placed at and/or adjacent to a site to be so treated.

For local administration, the glucocorticosteroid is delivered by any art known method at or adjacent to the site at which a local anesthetic was previously induced. In this way, additional doses and accumulation of potentially irritating or toxic amounts of local anesthetic are avoided. It is also contemplated that the local anesthesia is optionally repeatedly reactivated and/or prolonged by repeated administration or local release of an effective amount of a suitable glucocorticosteroid agent.

The methods and formulations according to the invention may be applied, e.g., topically. Thus, any pharmaceutically acceptable formulation suitable for topical administration, e.g., to the skin or mucosal surfaces may be employed for administration of a local anesthetic and/or a glucocorticoid agent according to the invention, either as a single formulation or in separate formulations for inducing topical local anesthesia. This is followed by topical administration of a formulation including a glucocorticoid in controlled release form, e.g., microspheres, in immediate release form or a mixture of controlled and immediate release glucocorticoid.

For internal administration, any pharmaceutically acceptable formulation for local implantation, infiltration or injection in proximity to a nerve, comprising an effective amount of a suitable local anesthetic, in immediate release and/or controlled release form, may be employed to provide localized anesthesia as needed. Slow release formulations and/or carriers, e.g.; emulsions, liposomes, gels, suspensions, gum matrices, and a wide variety of polymer formulations; known in the art include specially coated pellets, polymer formulations or matrices for surgical insertion or controlled release microparticles or microspheres for implantation, insertion or injection, wherein the slow release of the active medicament is brought about through controlled diffusion out of the matrix and/or selective breakdown of a polymer matrix. The formulation may optionally be coated with a special coating, film or barrier layer designed to control release of a local anesthetic agent by controlling its diffusion out of the formulation and/or by selective breakdown of the coating or selective breakdown of a matrix, if present.

Thus, the formulations and methods of the invention may be used in conjunction with any implantable, insert able or injectable delivery system known in the art, including but not limited to microspheres, microcapsules, gels, pastes, implantable rods, pellets, plates or fibers, and the like.

Similarly, formulations suitable for use in restoration of localized anesthesia according to the invention may be prepared as solutions or suspensions of glucocorticosteroids in immediate release or controlled release form, as described hereinabove for local anesthetic formulations. An effective amount of a glucocorticosteroid formulation may also be administered systemically, e.g., intravenously or orally, to provide for restoration of local anesthesia, but localized administration is preferred. As for controlled release local anesthetics, slow release formulations that can be used for recovery of localized anesthesia can be any suitable formulations that are known in the art, e.g., including specially coated pellets, polymer formulations or matrices for surgical insertion or as controlled release, e.g., microspheres, or, optionally, microcapsules for implantation, insertion or injection, wherein the slow release of the active medicament is brought about through controlled diffusion out of the matrix formulation, e.g., and/or selective breakdown of the coating of the preparation or selective breakdown of a polymer matrix.

In a preferred aspect, the slow release formulation is prepared as microspheres in a size distribution range suitable for local injection. The diameter and shape of the microspheres or other particles can be manipulated to modify the release characteristics. For example, larger diameter microspheres will typically provide slower rates of release and reduced tissue penetration and smaller diameters of microspheres will produce the opposite effects, relative to microspheres of different mean diameter but of the same composition. In addition, other particle shapes, such as, for example, cylindrical shapes, can also modify release rates by virtue of the increased ratio of surface area to mass inherent to such alternative geometrical shapes, relative to a spherical shape.

In a further aspect, the local anesthetic can be provided in a controlled release form and a glucocorticosteroid can also be included in the local anesthetic formulation. Thus, in this aspect, the invention provides microspheres containing both local anesthetic and at least one glucocorticosteroid, wherein the controlled release microspheres are formulated to begin releasing the glucocorticosteroid simultaneously with the release of the local anesthetic and/or after a predetermined time period post-injection, when it is desired to restore or prolong the initial local anesthesia. In a particular aspect of a combined local anesthetic-glucocorticosteroid formulation, pellets, spheroids and microspheres and the like can be prepared to comprise an outer layer of controlled release local anesthetic agent coated on a substrate comprising a glucocorticosteroid in immediate release or in controlled release form, in order to effect a predetermined order of release of the respective agents.

The artisan will appreciate that the pharmaceutically acceptable composition comprising a glucocorticosteroid agent can be administered by any art known method, including oral ingestion, systemic injection and local infiltration, infusion or injection. Thus, in addition to more conventional routes of administration, the reactivating glucocorticosteroid agent can be placed in a controlled release formulation from which release can be optionally initiated and controlled by a signal generated outside of the patient's body. This aspect of the present invention provides for greater convenience and reduced patient discomfort by providing control of local anesthesia without requiring further injections. Thus, simply by way of example, a single injection of controlled release local anesthetic and a signal-controlled glucocorticosteroid formulation can be administered, e.g., before a surgical procedure. If the patient is not uncomfortable after the procedure, no reactivation of the local anesthesia will be required. If, as the initial anesthesia wanes, it is determined that reactivation is desirable, the rate of release of the glucocorticosteroid agent from the formulation previously administered is increased by application of an external signal.

Such signal-controlled release formulations are known to the art and, simply by way of example, include polymer matrices embedded with small magnets which increase the rate of release of an incorporated active agent in the presence of oscillating magnetic fields (e. g., Edelman, 1993, Biomaierials 14(8):621–626; a hydrophilic polymer capable of a rapid increase in the rate of release of incorporated active agent upon the application of ultrasound (Miyazaki et al, 1988, Journal of Pharmacy & Pharmacology 40(10):716–717) and a hydrophilic polymer matrix capable of delivering an incorporated active agent at increased rates, upon exposure to microwave radiation (Mlyazaki et al., 1989, *Chemical & Pharmaceutical Bulletin* 27(1) 208–10). The artisan will, of course, appreciate that other signal-modulated polymer formulations are readily adaptable to the convenient practice of the present invention.

For formulations of local anesthetic and/or glucocorticosteroid agents, the diameter of injectable microspheres are sized for convenience in administration by local infiltration, injection, infusion or application. Preferably, the microspheres range in size from about 5 microns to about 200 microns in diameter. In a more preferred embodiment, the microspheres range in diameter from about 20 to about 120 microns.

The controlled release carrier and/or material should be biocompatible, e.g., safe for administration to a patient. In the case of polymeric materials, biocompatibility is enhanced by purification methods known to the art, e.g., recrystallization of either the monomers forming the polymer and/or the polymer using standard techniques.

In another embodiment, the carrier is a biocompatible, non-inflammatory and nonbiodegradable polymer such as, e.g., ethylene vinyl acetate ("EVA"). Such a nonbiocompatible polymer permits inserted or injected formulations to remain localized and able to be removed, intact, should that be required. Biodegradable carriers soften and lose their structural integrity over time, making the task of emergency removal difficult, if not impossible.

Polymers that are pharmaceutically acceptable, i.e., biocompatible, can be utilized as the controlled release material. Such polymers can be selected from a variety of sources including co-polymers of hydroxy acids such as lactic acid and glycolic acid, polyglycolic acid, polylactic acid, polyanhydrides, polyorthoesters, polycaprolactones, polyphosphazenes, polysaccharides, proteinaceous polymers, soluble derivatives of polysaccharides, soluble derivatives of proteinaceous polymers, polypeptides, polyesters, and polyorthoesters. The polysaccharides may be poly-1,4-glucans, e.g., starch glycogen, amylose and amylopectin, and the like. The hydrophilic or hydrophobic polymer may be a water-soluble derivative of a poly-1,4-glucan, including hydrolyzed amylopectin, hydroxyalkyl derivatives of hydrolyzed amylopectin such as hydroxyethyl starch (HES), hydroxyethyl amylose, dialdehyde starch, and the like. Optionally, the polymers are also biocompatible Preferred controlled release materials which are useful in the formulations of the invention include the polyanhydrides, co-polymers of lactic acid and glycolic acid wherein the weight ratio of lactic acid to glycolic acid is no more than 4:1 (i.e., 80% or less lactic acid to 20% or more glycolic acid by weight), and polyorthoesters containing a catalyst or degradation enhancing compound, for example, containing at least 1% by weight anhydride catalyst such as maleic anhydride. Other useful polymers include protein polymers'such as gelatin and fibrin and polysaccharides such as hyaluronic acid. Since polylactic acid takes at least one year to degrade in vivo, this polymer should be utilized by itself only in circumstances where such a degradation rate is desirable or acceptable.

Proteinaceous polymers may also be used. Proteinaceous polymers and their soluble derivatives include gelation biocompatible synthetic polypeptides, elastin, alkylated collagen, alkylated elastin, and the like. Biocompatible synthetic polypeptides also include poly-(N-hydroxyalkyl)-L-asparagine, poly-(N-hydroxyalkyl)-L-glutamine, copolymers of N-hydroxyalkyl-L-asparagine and N-hydroxyalkyl-L-glutamine with other amino acids. Suggested amino acids include L-alamine, L-lysine, L-phenylalanine, L-valine, L-tyrosine, and the like.

In embodiments where the biocompatible polymer comprises a gel, one such useful polymer is a thermally gelling polymer, e.g., polyethylene oxide, polypropylene oxide (PEO-PPO) block copolymer such as Pluronic® F127 from BASF Wyandotte. In such cases, the local anesthetic formulation may be injected via syringe as a free-flowing liquid, which gels rapidly above 30° C. (e.g., when injected into a patient). The gel system then releases a steady dose of local anesthetic at the site of administration.

In additional embodiments of the invention, the controlled release material, which in effect acts as a carrier for the local anesthetic and/or the glucocorticoid agent, can further include a bioadhesive polymer such as pectins (polygalacturonic acid), mucopolysaccharides (hyaluronic acid, mucin) or non-toxic lectins or the polymer itself may be bioadhesive, e.g., polyanhydride or polysaccharides such as chitosan.

Definitions or further descriptions of any of the foregoing terminology are well known in the art and may be found by referring to any standard biochemistry reference text such as "Biochemistry" by Albert L. Lehninger, Worth Publishers, Inc. and "Biochemistry" by Lubert Stryer, W.H. Freeman and Company, both of which are hereby incorporated by reference.

The aforementioned biocompatible hydrophobic and hydrophilic polymers are particularly suited for the methods and compositions of the present invention by reason of their characteristically low human toxicity and virtually complete biodegradability.

The term "microspheres" are defined for purposes of the present inventions as particles comprising local anesthetic and pharmaceutically acceptable controlled release material, e.g., the aforementioned polymeric materials (used as a controlled release carrier for the drug) which are preferably anywhere from about 20 microns to about 200 microns, and more preferably from about 45 to about 90 microns in diameter. The microspheres are preferably formed in such a size as to be injectable. For purposes of the present invention, the term "microsphere" encompasses "micropar- ticle" and "microcapsule". The polymeric material used in the and microspheres of the present invention preferably have a molecular weight from about 5,000 to about 200,000.

The polymeric material may be prepared by any method known to those skilled in the art. For example, where the polymeric material is comprised of a copolymer of lactic and glycolic acid, this copolymer may be prepared by the procedure set forth in U.S. Pat. No. 4,293,539 (Ludwig, et al.), hereby incorporated by reference. Basically, therein the copolymers are prepared by condensation of lactic acid and glycolic acid in the presence of a readily removable polymerization catalyst (e.g., a strong acid ion-exchange resin such as Dowex HCR-W2-H). The amount of catalyst is not critical to the polymerization, but typically is form about 0.01 to about 20 parts by weight relative to the total weight of combined lactic acid and glycolic acid. The polymerization reaction may be conducted without solvents at a temperature from about 100° C. to about 250° C. for about 48 to about 96 hours, preferably under a reduced pressure to facilitate removal of water and by-products. The copolymer is then recovered by filtering the molten reaction mixture to remove substantially all of the catalyst, or by cooling and then dissolving the reaction mixture in an organic solvent such as dichloromethane or acetone and then filtering to remove the catalyst.

Polyanhydrides may be prepared in accordance with the methods set forth in U.S. Pat. No. 4,757,128, hereby incorporated by reference. For example, polyanhydrides may be synthesized by melt polycondensation of highly pure dicarboxylic acid monomers converted to the mixed anhydride by reflux in:acetic anhydride, isolation and purification of the isolated prepolymers by recrystallization,. and melt polymerization under low pressure ($10^{-4}$ mm) with a dry icelacetone trap at a temperature between 140°–250° C. for 10–300 minutes. High molecular weight polyanhydrides are obtained by inclusion of a catalyst which increases the rate of anhydride interchain exchange, for example, alkaline earth metal oxides such as CaO, BaO and $CaCO_3$. Polyorthoester polymers may be prepared, e.g., as set forth in U.S. Pat. No. 4,070,347, hereby incorporated by reference.

Various commercially available poly (lactide-co-glycolide) materials (LGA) may be used in the preparation of the formulations, e.g., microspheres of the present invention. For example, poly(d,l-lactic-co-glycolic acid) are commercially available. A preferred commercially available product is a 50:50 poly (D,L) lactic co-glycolic acid having a mole percent composition of 50% lactide and 50% glycolide. Other suitable commercially available products are 65:35 DL, 75:25 DL, 85:15 DL and poly(d,l-lactic acid) (d,l-PLA). For example, poly(lactide-co-glycolides) are also commercially available from Boehringer Ingelheim (Germany) under its Resomer© mark, e.g., PLGA 50:50 (Resomer RG 502), PLGA 75:25 (Resomer RG 752) and d,l-PLA (resomer RG 206), and from Birmingham Polymers (Birmingham, Ala.). These copolymers are available in a wide range of molecular weights and ratios of lactic to glycolic acid.

The polymers utilized in the microspheres of the present invention may be prepared, e.g., by the condensation of lactic acid and glycolic acid in the presence of a readily removable polymerization catalyst. Such catalysts include strong acid ion-exchange resins in the form of beads or similarly hard structures which are easily removed by filtration or similar techniques. Further information concerning the preparation of the copolymers of the present invention is readily available to those skilled in the art, and may be ascertained from, e.g., U.S. Pat. No. 4,293,539 (Ludwig, et al.), hereby incorporated by reference.

Pharmaceutically acceptable polyanhydrides which are useful in the present invention have a water-labile anhydride linkage. The rate of drug release can be controlled by the particular polyanhydride polymer utilized and its molecular weight. The polyanhydride polymer may be branched or linear. Examples of polyanhydrides which are useful in the present invention include homopolymers and copolymers of poly(lactic acid) and/or poly(glycolic acid), poly[bis(p-carboxyphenoxy)propane anhydride] (PCPP), poly[bis(p-carboxy)methane anhydride] PCPM), polyanhydrides of oligomerized unsaturated aliphatic acids, polyanhydride polymers prepared from amino acids which are modified to include an additional carboxylic acid, aromatic polyanhydride compositions, and co-polymers of polyanhydrides with other substances, such as fatty acid terminated polyanhydrides, e.g., polyanhydrides polymerized from monomers of dimers and/or trimers of unsaturated fatty acids or unsaturated aliphatic acids.

Other polymers may be employed, as described in co-owned U.S. Pat. No. 5,922,340, which issued on Jul. 13, 1999, the disclosure of which is incorporated by reference herein in its entirety.

The biocompatible controlled release microspheres of the present invention may be prepared by any procedure known to those skilled in the art. Methods for the manufacture of microspheres include solvent evaporation, phase separation and fluidized bed coating.

Thus, in certain preferred embodiments, the microspheres may be obtained by utilizing a solvent extraction technique (reactor process) which involves dissolving the drug and the polymer in an organic solvent such as ethyl acetate. This solution thereby obtained (the dispersed phase) is added to a solution of, e.g., polyvinyl alcohol (PVA) in water (the continuous phase) with stirring. The emulsion thereby formed is then added to water in order to extract the solvent and to harden the mnicrospheres. The mixture is then filtered and the microspheres are dried. One appropriate method of drying is, e.g., under vacuum at room temperature. Optionally, the microsphere may be dried by a freeze drying process. The desired particle size fraction is then collected by sieving. The organic solvent utilized is preferably ethyl acetate; however, any pharmaceutically acceptable organic solvent may be utilized, such as acetone, ethanol, diethyl ether, methanol, benzyl alcohol, methylene chloride, petroleum ether or others. This procedure is particularly useful for preparing microspheres of e.g., bupivacaine base or freebase forms of glucocorticoids.

Alternatively, the microspheres of bupivacaine base and/or glucocorticoid may be prepared by dissolving the drug and polymer in ethyl acetate and thereafter spray drying the solution.

In instances where the microspheres are to. incorporate drugs which are very water soluble and insoluble in ethyl acetate, such as bupivacaine HCl and/or water soluble glucocorticoids, the microspheres may be prepared using a coacervation/phase separation rather than the solvent extraction technique described above. However, the solvent extraction technique can be used with e.g., bupivacaine HCl and/or water soluble glucocorticoids due to its low water solubility at pH 7.4 and above. The coacervation/phase separation technique utilized involves dissolving the polymer in ethyl acetate and suspending micronized bupivacaine HCl in the solution. Silicone oil is then added to form the microspheres. This mixture is then added to heptane to harden the microspheres, which are then separated by filtration. The microspheres are dried under a vacuum at room temperature. The desired particle size fraction is then collected by sieving.

Alternatively, microspheres prepared using bupivacaine HCl and/or glucocorticoids may be accomplished by suspending the drug in a solution of polymer in ethyl acetate or in methylene chloride and methanol and spray drying.

Further, the drug or drugs may be dissolved in water, and the polymer may be dissolved in ethyl acetate. The water phase then can be added to the organic phase and either homogenized or sonicated to yield a W/O emulsion. The drug being in the water phase would then be surrounded by polymer (oil phase). This is then poured into PVA solution in water with homogenization to form a W/O/W emulsion; The solvent diffuses out, leaving microspheres. Additional cold water can be added to harden the microspheres. This process may yield more uniform nicrospheres without requiring micronization of the drug. Also, as the drug will be surrounded by polymer, the release of the drug may be more uniform and would be diffusion-controlled.

In fluidized bed coating, the drug is dissolved in an organic solvent along with the polymer. The solution is then. processed, e.g., through a Wurster air suspension coater apparatus to form the final microcapsule product.

The ultimate drug content of the microspheres according to the present invention may be varied substantially, depending upon whether a high load or a low load formulation procedure is utilized. In certain preferred embodiments (e.g., where the drug is bupivacaine), the drug content of the microspheres, by weight, may be from about 0.1 to about 90%, preferably from about 30% to about 90% and more preferably from about 60% to about 85% of the total weight of the micro-sphere, and most preferably, about 75% by weight.

In one preferred embodiment of the present invention, the drug included in the microspheres is a local anesthetic either of the ester or amide type. Suitable local anesthetics of the ester type include the benzoic acid esters (e.g., piperocaine, meprylcaine, isobucaine), the para-aminobenzoic acid esters (e.g., procaine, tetracaine, butethamine, propoxycaine, chloroprocaine); meta-aminobenzoic acid esters (e.g., metabutethamine, primacaine), paraethoxybenzoic acid esters (e.g., parethoxycaine), and their pharmaceutically acceptable salts. The non-esters include, e.g., lidocaine, mepivacaine, pyrrocaine, prilocaine, bupivacaine, etidocaine, pharmaceutically acceptable salts. A most preferred local anesthetic is bupivacaine.

In certain preferred embodiments of the present invention, the microspheres incorporate bupivacaine as the drug in an amount from about 45% to about 70% by weight, the copolymer being PLGA 50:50 of a molecular weight from about 5,000 to about 200,000.

The microspheres of the present invention preferably provide a sustained action in the localized area to be treated. For example, when the drug included in the microspheres is bupivacaine, it would be desirable that such a formulation could provide localized anesthesia to the area in question for a period of one day, two days, three days, or longer. When the incorporated drug is a glucocorticoid, it would be desirable that the formulation could provide reactivation and/or prolongation for a period of e.g., 8 hours, 1, 2, 3 or up to 4 days or longer. The formulations can therefore, of course, be modified in order to obtain such a desired result.

The microspheres of the present invention may be utilized as a controlled release formulation to deliver local anesthetic, glucocorticoid reactivating agent and/or combinations of the same, preferably by incorporating an effective amount of the same into a pharmaceutically acceptable solution (e.g., water) or suspension for injection. The final reconstituted product viscosity may be in a range suitable for the route of administration. In certain instances, the final reconstituted product viscosity may be, e.g., about 35 cps. Administration may be via the subcutaneous or intramuscular route. However, alternative routes are also contemplated, and the formulations may be applied to the localized site in any manner known to those skilled in the art, such that a localized effect is obtained. The microspheric formulations of the present invention can be implanted at the site to be treated. Thereby, the formulations of the present invention, when including a local anesthetic, may be used in the control of post-operative pain.

The dosage of the controlled release microsphere formulations of the present invention is dependent upon the kind and amount of the drug to be administered, the recipient animal, and the objectives of the treatment. For example, when the drug included in the microspheres of the present invention is bupivacaine, the formulation may include, e.g., from about 0.5 to about 2 mg/kg body weight. Since the formulations of the present invention are controlled release, it is contemplated that formulations may include much more than usual immediate release doses, e.g., as much as 450 mg/kg bupivacaine or more.

The effective dose of bupivacaine, or an amount of another local anesthetic sufficient to provide equivalent potency (i.e., equally effective doses), can range from about 1 to about 50 mg of bupivacaine injected or inserted at each site where the release of a local anesthetic agent is desired.

In certain preferred embodiments, the dose of bupivacaine in the controlled release dosage form of the invention is sufficient to provide a controlled release of about 1 to about 30 mg of local anesthetic per hour at the release site for the desired duration of anesthesia, e.g., a time period ranging from about 8 to about 4 days or more, from about 1 to about 24 hours, or from about 1 to about 12 hours or even from about 1 to about 8 hours.

It is possible to tailor a system to deliver a specified loading and subsequent maintenance dose by manipulating the percent drug incorporated in the polymer and the shape of the matrix or formulation, in addition to the form of local anesthetic (e.g., free base versus salt) and the method of production. The local anesthetic is incorporated into the polymer or other controlled-release formulation in a percent loading between 0.1% and 90%, by weight, preferably between about 5% and 75%, by weight and, more preferably from about 60% to about 80% by weight.

The amount of drug released per day increases proportionately with the percentage of drug incorporated into the formulation, e.g., matrix (for example, from 5 to 10 to 20%). In one preferred embodiment, polymer matrices or other formulations comprising from about 70% to about 75% by weight, of local anesthetic, are utilized, although it is possible to incorporate substantially more drug, depending on the drug, the method used for making and loading the formulation, and the polymer. It should be noted that in a preferred embodiment, formulations prepared according to the present invention, e.g., as nicrospheres, can bee loaded with, e.g., 75% by weight of bupivacaine free base, and nevertheless provide a controlled release of bupivacaine, in vitro, without any "dose-dumping" effect.

A desired release profile of an incorporated drug or drugs can be achieved by using a mixture of microspheres formed of polymers having different release rates and/or different percent loading of local anesthetic and/or glucocorticosteroid agent, for example, polymers releasing in one day, three days, and one week, so that linear release is achieved even when each polymer per se does not release linearly over the same time period. In addition, a mixture of microspheres having one or more different local anesthetic agents, having the same or different controlled release profile, can be utilized to provide the benefits of different potencies and spectrum of activity during the course of treatment.

The biocompatible controlled release materials may also be used in order to, prepare controlled release local anesthetic implants. The implants may be manufactured, e.g., by compression molding, injection molding, screw extrusion and hot melt methods, whereby the local anesthetic agent is loaded into the polymer. Implantable fibers can be manufactured, e.g., by blending the local anesthetic agent with the controlled release material and then extruding the mixture, e.g., under pressure, to thereby obtain biocompatible fibers. In certain preferred embodiments, the glucocorticosteroid agent may be incorporated into the implant, or may be coated onto a surface of the implant.

In other embodiments of the invention, the controlled release material comprises an artificial lipid vesicle, or liposome. Liposomes are well known in the art as carriers of bioactive or pharmacologically active substances such as drugs. Liposomes as described herein will vary in size. Preferably, the liposomes have a diameter between 100 nm and 10 microns or greater. A wide variety of lipid materials may be used to form the liposomes including natural lecithins, e.g., those derived from egg and soya bean, and synthetic lecithins, the proviso being that it is preferred that the lipids are non-immunogenic and biodegradable. Also, lipid-based materials formed in combination with polymers may be used, such as those described in U.S. Pat. No. 5,188,837 to Domb, (incorporated by reference. herein).

Examples of synthetic lecithins which may be used together with their respective phase transition temperatures, are di-(tetradecanoy)phosphatidylchoeline (DTPC) (23° C.), di-(hexadecanoyl)phosphatidylcholine (DHPC) (41° C.) and di-(octandecanoyl)phosphatidylcholine (DOPC) (55° C.). Di-(hexadecanoyl) phosphatidycholine is preferred as the sole or major lecithin, optionally together with a minor proportion of the di-(octadecanoyl) or the di-(tetradecanoyl) compound. Other synthetic lecithins which may be used are unsaturated synthetic lecithins, for example, di-(oleyl) phosphatidyl-choline and di-(inoleyl)phosphatidylcholine. In addition to the main liposome-forming lipid or lipids, which are usually phospholipids, other lipids (e.g. in a proportion of 5–40% w/w of the total lipids) may be included, for example, cholesterol or cholesterol stearate, to modify the structure of the liposome membrane, rendering it more fluid or more rigid depending on the nature of the main liposome-forming lipid or lipids.

Liposomes may be prepared by dissolving an appropriate amount of a phospholipid or mixture or phospholipids together with any other desired lipid soluble components (e.g., cholesterol, cholesterol stearate) flowing in a suitable solvent (e.g., ethanol) and evaporating to dryness. An aqueous solution of the local anesthetic, optionally with glucocorticosteroid agent, may then be added and mixed until a lipid film is dispersed. The resulting suspension will contain liposomes ranging in size, which may then fractionated to remove undesirable sizes, if necessary. This fractionation may be effected by column gel chromatography, centrifugation, ultracentrifugation or by dialysis, as well know in the art.

The above method of preparation of liposomes is representative of a possible procedure only. Those skilled in the art will appreciate that there are many different methods of preparing liposomes, all of which are deemed to be. encompassed by the present disclosure.

It is possible to tailor a system to deliver a specified loading and subsequent maintenance dose of local anesthetic by manipulating the percent drug incorporated in a controlled release carrier. When the controlled release carrier is a polymer and/or matrix formulation, it is possible to manipulate and the shape of the matrix or formulation, in addition to the form of local anesthetic (e.g., free base versus salt) and the method of production. The amount of drug released per day increases proportionately with the percentage of drug incorporated into the formulation, e.g., matrix (for example, from 5 to 10 to 20%). In the preferred embodiment, polymer, matrices or other formulations with about 75% drug incorporated are utilized, although it is possible to incorporate substantially more drug, depending on the drug, the method used for making and loading the device, and the polymer.

In a preferred embodiment, the controlled release formulation comprising local anesthetic provides, in vitro, from about 10 to about 60 percent release of local anesthetic after 24 hours, from about 20 to about 80 percent release after 48 hours and from about 40 to about 100 percent release after 72 hours.

In a more preferred embodiment, the controlled release formulation comprising local anesthetic provides a preferred rate of release, in vitro, from about 25 to about 40 percent release of local anesthetic after 24 hours, from about 40 to about 50 percent release after 24 hours and from about 45 to about 55 percent release after 72 hours and 80 to 100 percent cumulative release is provided after about 280 hours.

The initial local anesthesia, can be induced by administration of an anesthetically effective amount of a local anesthetic agent or a mixture of local anesthetic agents. Optionally, the initial local anesthesia can be induced by administration of an anesthetically effective amount of a local anesthetic agent or a mixture of local anesthetic agents together with a glucocorticoid agent or a mixture of glucocorticoid agents.

The time period during which a glucocorticoid agent. can be administered for reactivation of local anesthesia ranges from about 1 hour after administration of the initial local anesthetic dose to about 72 hours or longer. In particular, the time period during which successful reactivation can be initiated ranges from about 1 hour after administration of the initial local anesthetic dose to about 72 hours, or more. More particularly, the time period during which successful reactivation can be initiated ranges from about 1 to about 24 hours, from about 1 to about 12 hours, from about 1 to about 6 hours, from about 1 to about 4 hours, from about 4 to about 72 hours and from about 4 to about 24 hours, after the time that the (e.g., first) local anesthetic was administered.

In another aspect, when the local anesthetic effect is reactivated or restored by the use of an glucocorticosteroid agent, the total duration of the obtained local anesthesia ranges from about 1.1 to about 14 fold, or more, of the duration of local anesthesia induced by controlled release local anesthetic without glucocorticosteroid enhancement. In a preferred embodiment, the methods, the prolongation ranges from about 6 to about 13 fold of the duration of local anesthesia induced by controlled release local anesthetic without glucocorticosteroid enhancement. The duration, measured from the time of administration of the local anesthetic, of the reactivated local anesthesia ranges from about 0.1 to about 72 hours or greater. In particular, the duration, measured from the time of administration of the reactivating composition, of the reactivated local anesthesia ranges from about 1 to about 48 hours or greater. Further, the duration of the local anesthetic effect reactivated by a glucocorticosteroid ranges from about 8 to about 30 hours, from the time of administration of the local anesthetic.

The rate of release of local anesthetic agent, glucocorticosteroid agent or other drugs incorporated into the controlled release formulations according to the invention will also depend on the solubility properties of the selected local anesthetic, glucocorticosteroid or other. drug. The greater the solubility in water, the more rapid the rate of release in tissue, all other parameters being unchanged. For example, those local anesthetic agents having pH dependent solubility will be released more rapidly at a pH lower than the pKa value for each such compound. Thus, the formulation may be optimized for the desired local anesthetic release rate by selecting local anesthetic agents having a desired water solubility in tissue, e.g., at tissue pH. Thus, a local anesthetic agent that is more soluble at acid pH will have a faster release rate in a relatively acidic (e.g., pH less than about 7.2) tissue. For example, in one embodiment, the formulation will have released, in vitro, at least 70 percent of a local anesthetic at 48 hours at about pH 6 and will have released at least 40 percent of a local anesthetic at a pH ranging from about 7.4 to about 8, at 48 hours. Other combinations are pH independent in their release.

Glucocorticosteroids and synthetic analogs that are useful to prolong the duration of anesthesia include glucocorticosteroids such as dexamethasone, cortisone, prednisone, hydrocortisone, beclomethasone dipropionate, betamethasone, flunisolide, methylprednisone, paramethasone, prednisolone, triamcinolone, alclometasone, amcinonide, clobetasol, fludrocortisone, diflorasone diacetate, fluocinolone acetonide, fluocinonide, fluorometholone, flurandrenolide, halcinonide, medrysone and mometasone and pharmaceutically-acceptable mixtures and salts of the same, and others that are routinely administered orally or by injection.

In a preferred aspect, an amount of a glucocorticosteroid agent effective to restore or reactivate a previously administered local anesthesia is administered when the previous anesthesia begins to wane. In another preferred aspect, glucocorticosteroid agent is administered after the previous local anesthesia has substantially or fully worn off. For example, an effective amount of a composition that includes a glucocorticosteroid agent or mixtures of such agents is administered at time ranging from about 1 to about 72 hours, or more, from about 1 to about 24 hours or more, from about 1 to about 12 hours, and from about 1 hours to about 2 hours, after the local anesthesia begins to subside or wear off.

When the glucocorticosteroid agent is included in a controlled release formulation, alone or further comprising local anesthetic, it has been found that useful loadings of glucocorticosteroid agent are from 0.001 to 30% by weight of the dosage form or about 0.005% to about 13% relative to the weight of the local anesthetic in order to provide prolonged release, e.g., for from 1 hour to 100 hours, or more or from, e.g., about 1 hour to about 72 hours, from about 1 hour to about 24 hours, from about 1 hour to about 8 hours and from about 1 hour to about 4 hours of controlled release.

In those instances where the glucocorticosteroid agent is dexamethasone, it is preferred that the dexamethasone comprises from, e.g., about 0.005 to about 0.5% of the controlled release formulation. Of course, the dosages of other glucocorticosteroids must be adjusted relative to the potency of dexamethasone. The dosage must be low enough to avoid toxicity. In one aspect, the combination of a glucocorticosteroid agent and a local anesthetic in a single controlled release formulation is designed for sequential release of first the local anesthetic and then the glucocorticosteroid agent.

When the formulation for inducing the initial local anesthesia is in injectable form, and at least a portion of the glucocorticosteroid agent is included in the aqueous injection medium, the amount of glucocorticosteroid. agent is from, e.g., about 0.001% to about 20% relative to the weight of the local anesthetic. When the glucocorticosteroid agent is dexamethasone that is included in the injection media, it is preferred that the dexamethasone be from, e.g., about 0.01% to about 1.3% or more, relative to the weight of the local anesthetic.

The examples demonstrate that glucocorticosteroid agents such as dexamethasone restore or reactivate local anesthesia in vivo. Potential applications include any condition for which reactivation of previously administered localized anesthesia is desirable. This includes both anesthesia for the relief of pain and motor symptoms as well as anesthesia for other medical purposes. The formulations and methods according to the invention can be used to provide intermittent and/or two to five day intercostal blockade or anesthetic effect for thoracotomy, or longer term intercostal blockade or anesthetic effect for thoracic post-therapeutic neuralgia, lumbar sympathetic blockade or anesthetic effect for reflex sympathetic dystrophy, or three-day ilioinguinal/ iliohypogastric blockade or anesthetic effect for hernia repair. Other potential applications include obstetrical or gynecological procedures. Yet further potential applications include providing localized temporary sympathectomy, e.g., blockade or anesthetic effect of sympathetic or parasympathetic ganglia to treat a variety of autonomic diseases, including circulatory dysfunction or cardiac dysrhythmias. The formulations may also be used to treat trigeminal neuralgia and other diseases of the cranial nerves as well as to provide temporary anesthesia to treat localized muscle spasm and treatment of retrobulbar conditions, e.g., eye pain.

Other uses include intra-operative administration in order to reduce pain during and after the operative procedure, especially for plastic surgery procedures where prolonged anesthesia will enhance the outcome. These are merely examples, and additional uses for both human and veterinary practice are immediately apparent to the artisan.

Methods of Administration

In a preferred method of administration a dosage form, e.g., microspheres, are administered by injection into a site where local anesthetic agent is to be released to provide an initial localized anesthesia. Microspheres may be e.g., applied topically, infiltrated, infused or injected through a syringe or a trochar. Pellets or slabs may be surgically placed into a site where release of oral anesthetic agent is desired.

As described below, microspheres according to the invention can be administered. alone or in combination with a controlled release formulation and/or a solution including a steroidal anti-inflammatory or other glucocorticosteroids in an amount effective to prolong the duration of local anesthesia. Alternatively, the microspheres include an amount of steroidal anti-inflammatory effective to prolong and/or reactivate a local anesthesia.

In another alternative, one or more glucocorticosteroids can be administered before, simultaneously with or after administration of the controlled release local anesthetic, wherein the glucocorticosteroid is formulated into a separate microsphere formulation for controlled release. The controlled release rate for the glucocorticosteroids may be the same as or different than the controlled release rate for the local anesthetic. In a further embodiment, it has been found that an additional dose of glucocorticosteroid may also be administered as an injectable solution, in an injectable carrier or in- a controlled release carrier to the nerve to be treated after the controlled release local anesthesia has worn off, in order to reactivate the initial anesthesia without the co-administration of additional local anesthetic.

The microspheres may be prepared from PLGA polymers ranging from, for example, PLGA in a ratio of 50:50, 65:35 or 75:25. An optimum composition has been determined to be PLGA 65:35.

The artisan will appreciate that, as with all local anesthetics, the dosage of local anesthetic containing microspheres will vary and will depend, simply by way of example, upon the area to be anesthetized, the vascularity of the tissues, the number of neuronal segments to be treated, the size and weight of the patient (e.g., veterinary practice, human child, human adult) individual tolerance and the technique of anesthesia. Of course, under normal circumstances, the lowest dosage need to provide effective anesthesia should be administered.

The microspheres, formulated with, e.g., PLGA 65:35 microspheres are administered in a dose ranging from, for example, 1 through 450 mg per kg of body weight, of microspheres 75% (w/w) loaded with a local anesthetic such as bupivacaine, per kg of body weight. In a preferred embodiment the dose ranges from 5 through 250 mg of microspheres/kg of body weight. In a more preferred embodiment the dose ranges from about 10 to about 150 mg of microspheres/kg of body weight, with PLGA 65:35.

An-effective dose of a local anesthetic, such as bupivacaine, is typically administered in microspheres comprising, e.g., 75% by weight bupivacaine, and can range from about 0.5 to about 1000 mg, or more, of bupivacaine, depending on the site to be anesthetized, the number of segments to be anesthetized and the patient, as discussed above. Preferably, a dose ranging from about 1 mg to about 500 mg of bupivacaine is administered, or even a dose ranging from about 5 mg to about 100 mg of bupivacaine is administered at the site and/or sites to be anesthetized.

Certainly, the artisan will appreciate the fact that the dose ranges mentioned above are based on the potency of bupivacaine, and that exact effective dosages will vary with the particular relative potency and pharmacokinetics of each local anesthetic and will be able to readily adjust the dose according to the degree of: anesthesia experienced by the patient.

The formulation described herein can also be used to administer local anesthetic agents that produce modality-specific anesthesia, as reported by Schneider, et al., *Anesthesioloy*, 74:270–281 (1991), or that possess physical-chemical attributes that make them more useful for sustained release then for single injection anesthesia, as reported by Masters, et al., *Soc. Neurosci. Abstr.*, 18:200 (1992), the teachings of which are incorporated herein.

Administration of formulations according to the invention may require the use of a vehicle, e.g., any vehicle that is pharmaceutically acceptable for the desired route of administration. Thus, for topical administration, the formulations prepared according to the invention comprising local anesthetic and/or glucocorticoid may be dissolved (e.g., for immediate release forms) or suspended (e.g., for microparticles) in vehicles .including buffered. solutions, e.g, saline solution, including, e.g, hypotonic and/or buffered saline, as well as in creams, ointments, oils, emulsions, liposomes and the like and/or any other art-known pharmaceutically acceptable topical vehicle. For administration by injection and/or infiltration, the formulations according to the invention may be suspended (e.g., for microparticles), or dissolved (e.g., for immediate release forms), in any art-known vehicle suitable for injection and/or infiltration. Such vehicles include, simply by way of example, isotonic saline, buffered or unbuffered and the like and/and may optionally include any other, art known ingredients or agents, e.g., colorants, preservatives, antibiotics, epinephrine and the like. A more-complete listing of art-known vehicles for i administration of formulations topically, by systemic administration and/or local injection and/or infiltration is provided by reference texts that are standard in the art, for example, REMINGTON'S PHARMACEUTICAL SCIENCES, 16th Edition, 1980 and 17th Edition, 1985, both Published by Mack Publishing Company, Easton, Pa., the disclosures of which are incorporated by reference herein in their entireties.

Clinical Utility

It will also be appreciated that the local anesthetic formulations and methods according to the invention can generally employed in any art known localized procedures for anesthetizing a patient. For example, for surface anesthesia, microsphere suspensions or other forms of controlled release carrier, e.g., microsphere, cellulose based polymers and/or gum matrices in paste form, suitable for topical application, are used to anesthetize mucous membranes, skin and for ophthalmological use. Effective amounts of glucocorticoid agents can be included with the topical controlled release formulation or, optionally, at least a portion of the glucocorticoid agent can be separately administered in controlled release form, immediate release form and/or a combination thereof.

In addition, the local anesthetic formulations and methods according to the invention can be used for infiltration anesthesia, wherein a formulation suitable for injection is injected directly into the tissue requiring anesthesia. For example, an effective amount of the formulation in injectable form is infiltrated into a tissue area that is to be incised or otherwise requires local anesthesia. In addition, the local anesthetic formulations and methods according to the invention can be used for field block anesthesia, by injecting an effective amount of the formulation in injectable form in such a manner as to interrupt nerve transmission proximal to the site to be anesthetized. For instance, subcutaneous infiltration of the proximal portion of the volar surface of the forearm results in an extensive area of cutaneous anesthesia that starts 2 to 3 cm distal to the site of injection. Simply by way of example, the same effect can be achieved for the scalp, anterior abdominal wall and in the lower extremities. Effective amounts of glucocorticoid agents can be included with injectable controlled release formulation or, optionally, at least a portion of the glucocorticoid agent can be separately administered in controlled release form, immediate release form and/or a combination thereof.

Further, for even more efficient results, the local anesthetic formulations and methods according to the invention can be used for nerve block anesthesia. For example, an effective amount of the formulation in injectable form is injected into or adjacent to individual peripheral nerves or nerve plexuses. Injection of an effective amount of a local anesthetic formulation according to the invention into mixed peripheral nerves and nerve plexuses can also desirably anesthetize somatic motor nerves, when required. The formulations and methods according to the invention can also be used for intravenous regional anesthesia by injecting a pharmacologically effective amount of microspheres in injectable form into a vein of an extremity that is subjected to a tourniquet to occlude arterial flow.

Further still, spinal and epidural anesthesia using formulations, e.g., injectable microspheres and methods according to the invention will be appreciated by the artisan to be within the scope contemplated by the present invention.

The formulation described herein can also be used to administer local anesthetic agents that produce modality-specific anesthesia, as reported by Schneider, et al., *Anesthesiology*, 74:270–281 (1991), or that possess physical-chemical attributes that make them more useful for sustained release then for single injection anesthesia, as reported by Masters, et al., *Soc. Neurosci. Abstr.*, 18:200 (1992), the teachings of which are incorporated herein.

DETAILED DESCRIPTION OF THE PREFERRED EMBODIMENTS

The following non-limiting examples illustrate the preparation of the formulations according to the invention and the effects of local anesthetic and glucocorticosteroid agents alone and in combination.

EXAMPLE 1

In vivo and In vitro Release Profile of Polymer Local Anesthetic Matrices containing Anesthetic in Combination with Glucocorticoid In vitro release profiles and the in vivo effects of bupivacaine and dexamethasone release were determined as follows.

Methods and Materials

Implants

Copolymers of 1,3-bis(p-carboxy-phenoxy)propane and sebacic acid (20:80) were synthesized and recrystallized to remove impurities. Polymer local anesthetic matrices were prepared in the form of pellets containing 10% and 20% L-cis-hydroxyproline (CHP) by weight of CPP:SA (20:80) copolymer or containing 20% crystalline bupivacaine-HCL by weight of CPP:SA 20:80 copolymer were produced using the hot melt procedure. Polymer local anesthetic matrices incorporating both bupivacaine and dexamethasone were synthesized via. the hot melt procedure in the form of pellets, using a uniform mixture of dexamethasone and bupivacaine formed by combining dexamethasone dissolved in 95% ethanol with bupivacaine dissolved in 95% ethanol. The solution was air-dried under the hood at room temperature until the ethanol evaporated and left behind a well-dispersed mixture of dry crystalline dexamethasone and bupivacaine. The crystalline mixture was pulverized under mortar and pestle and combined with copolymer. Control pellets contained only CPP:SA (20:80) copolymer and all pellets were synthesized with large bore Teflon® (polytetrafluoroethylene) tubing.

Two different dosage sets of dexamethasone/bupivacaine pellets were produced: high dose (hd) dexamethasone and low dose (ld) dexamethasone. Hd-dexamethasone/bupivacaine pellets contained approximately 60 $\mu$g dexamethasone per pellet. Ld-dexamethasonebupivacaine pellets contained approximately 15 $\mu$g per pellet. Both sets contained 20% bupivacaine by weight.

In vitro Studies

Tritium labeled dexamethasone ($^3$H-dexamethasone) was purchased from New England Nuclear Corporation (Boston, Mass.). An aliquot consisting of $10^7$ counts was added to a mixture of 200 $\mu$g unlabeled dexamethasone and 190 mg bupivacaine dissolved in 95% ethanol. This solution was air-dried under the hood at room temperature until the ethanol evaporated and left behind a well-dispersed mixture of dry crystalline $^3$H-labeled dexamethasone, unlabeled dexamethasone and bupivacaine. This dry crystalline mixture was pulverized under mortar and pestle and combined with 650 mg CPP:SA (20:80) copolymer. All $^3$H-dexamethasone/unlabeled dexamethasone/bupivacaine pellets were synthesized using large bore Teflon® tubing. Each pellet was placed in 5 mL of sterile 1×PBS (phosphate-buffered saline) containing 1% sodium azide and incubated at 37° C. The incubated 1×PBS media was removed and stored at −20° C., and replaced with 5 ml of fresh sterile 1×PBS at 2 h, 6 h and 24 h time points and then once daily thereafter for 3 weeks. The $^3$H released was counted using a liquid scintillation counter (Rackbeta 1214).

In Vivo Studies

Animals were implanted with 3 hd-dexamethasone/bupivacaine pellets or 3 ld-dexamethasone/bupivacaine pellets on the experimental side. Control animals were implanted with 3 control pellets on the control side.

Surgery

All animals were anesthetized with 3.5%–4.0% halothane in oxygen and maintained with 1.5%–2.0% halothane. Anesthesia was achieved within 3–5 minutes post induction. Animals were tested by pinching of tailbase and pawpads to confirm the anesthetic state. The thigh area was shaved and an incision was made directly below the greater trochanter. The hamstrings were gently divided by blunt dissection to expose the sciatic nerve. Pellets were placed adjacent to the sciatic nerve under direct vision in the fascial plane deep to the hamstrings and the site was irrigated with 0.5 cc of antibiotic solution (5000 units/mL penicillin G sodium and 5000 ug/mL streptomycin sulfate) to prevent infection. The most superficial facial layer was closed with a single suture. The edges of the outer skin were approximated and closed with one to two surgical staples.

For all rats, drug-containing pellets were implanted on the experimental side. The control (contralateral) side varied among the groups.

Necropsy

For autopsy, the skin of the dorsal thigh was removed. A midline transverse cut-was made through each successive layer of hamstring muscle. A 3 cm segment of the sciatic nerve was removed from its exit point at the greater sciatic foramen to its branching point above the dorsal aspect of the knee joint. For light microscopy, a segment was fixed in 10% buffered formalin.

Histology

Nerves: For evaluation of sciatic nerves, cross-sections were processed, embedded in paraffin and sectioned at 2 $\mu$m and stained with hematoxylin eosin. 5–10 sections were studied via light microscopy by a pathologist in a blinded manner. Each cross-section was evaluated for (1) epineural inflammation, (2) epineural fibrosis, and (3) subperineural fibroblasts. Each parameter was rated on a severity scale of 0–4. A score of 0=no change, 1=mild, 2=moderate, 3=moderate-severe and 4 severe.

Results

In Vitro Release of Dexamethasone

The release of dexamethasone from pellets was nearly linear for the first 8 days and eventually reached a plateau by Day 21. Approximately 60% of dexamethasone was released from pellets by Days 7–8 and by Day 21, 97% of dexamethasone was released.

In vivo Results

Sensory and Motor Anesthesia Among Animals Treated with dexamethasone and CHP

Animals implanted with ld-dexamethasone/bupivacaine pellets had the longest sensory and motor blockade or anesthesia effect. Sensory blockade or anesthesia effect lasted for a period of 6–7days with maximum blockade intensity (latency=12 sec) observed on days 1–5 in all animals. Motor blockade or anesthesia effect lasted for 6–8 days with the densest motor blockade or anesthesia effect seen on day 1–5. All animals returned to baseline on Day 8. Rats implanted with hd-dexamethasone/bupivacaine pellets also had sensory blockade or anesthesia effect lasting 6–7 days. However, maximum blockade intensity was observed only on days 1–2 in all rats. A plateau of dense blockade (latency=7–11 sec) was seen on days 3–5. Motor blockade or anesthesia effect lasted for 3–5 days with the . densest motor blockade occurring on day 1–2. Group 4 animals (control group. receiving large bore bupivacaine pellets) had sensory blockade or. anesthesia effect lasting 5–6 days. There were no time points when all animals had maximum blockade intensity simultaneously. However, dense sensory blockade or anesthesia effect (latency=7–11 sec) was observed on days 14 in all animals. Motor blockade or anesthesia effect lasted 3–6 days with densest blockade seen on Days 1–2. Rats, who were implanted with hd-dexamethasone pellets, showed no sensory and motor blockade or anesthesia effect, and all time points could not be distinguished from baseline. Rats who were implanted with 10% CHP polymer local anesthetic matrix pellets plus bupivacaine pellets, 20% CHP pellets and plus bupivacaine pellets, and bupivacaine pellets alone, respectively, all displayed similar sensory blockade or anesthesia effect durations and intensities. All groups showed sensory blockade or anesthesia effect durations of 2–4 days with dense blockade or anesthesia effect seen on Day 1 and the majority of rats returning to baseline on Days 2–4. Duration of motor blockade or anesthesia effect lasted for 1–2 days with the densest blockade or anesthesia effect observed primarily on day 1.

Plasma Assays for ACTH and Corticosterone

Plasma assays showed no difference in ACTH and corticosterone levels compared to normal values of rats taken at the same period of day and under similar stress-level conditions.

EXAMPLE 2

Methods For Conducting Tests

The following methods were utilized in the in vivo studies on rats. All tests were conducted at standard room temperature, e.g., 22–25° C.

Anesthesia Tests

Motor Anesthesia

The rats were behaviorally tested for sensory and motor anesthesia in a quiet observation room. Testing was only performed in rats showing appropriate baseline hot plate latencies after at least-one week of testing. In all testing conditions, the experimenter recording the behavior was unaware of the side containing the local anesthetic. To assess motor anesthesia, a 4-point scale based on visual observation was devised: (1) normal appearance, (2) intact dorsiflexion of foot with an impaired ability to splay toes when elevated by the tail, (3) toes and foot remained plantar flexed with no splaying ability, and (4) loss of dorsiflexion, flexion of toes, and impairment of gait. For graphing clarity, partial motor anesthesia equals a score of 2 and dense motor anesthesia is a score of either 3 or 4.

Sensory Anesthesia

Sensory anesthesia was measured by the time required for each rat to withdraw its hind paw from a 56° C. plate (IITC Life Science Instruments, Model 35-D, Woodland Hills, Calif.). The rats were allowed to adjust to their surroundings in a quiet room for at least 30 minutes before testing. The rats were held with a cloth gently. wrapped above their waist to restrain the upper extremities and obstruct vision. The rats were positioned to stand with one hind paw on a hot plate and the other on a room temperature plate. With a computer data collection system to (Apple IIe with a footpad switch), latency to withdraw each hind paw to the hot plate was recorded by alternating paws and allowing at least fifteen seconds of recovery between each measurement. If no withdrawal occurred from the hot plate within 12 seconds, the trial was terminated to prevent injury and the termination time was recorded. Testing ended after five measurements per side, the high and low points were disregarded, and the mean of the remaining three points was calculated for each side. Animals were handled in accordance with institutional, state and federal guidelines.

No rats were observed to have inflammation or blisters. Rats were tested for at least two weeks prior to surgery to achieve a consistent baseline latency, and testing continued for two weeks after surgery to confirm complete recovery from sensory anesthesia Motor anesthesia (e.g., blockade) was rated on a 4-point scale Animals with a motor blockade or anesthesia effect of 4 had a clubbed hindpaw and usually dragged their affected leg when walking. Motor blockade or anesthesia effect 3 animals walked normally but had toes that failed to splay when the animal was lifted. Animals with motor blockade or anesthesia effect of 2 showed toes that splayed but not as fully as normal or motor blockade or anesthesia effect 1 animals.

Necropsy and Histology

Animals were sacrificed two weeks after implantation. Sections of sciatic nerve approximately 2–3 cm in length, adjacent and proximal to the implants, were preserved. in 10% formalin solution (24 mM sodium phosphate, pH 7). Sections were then embedded in paraffin, stained with hematoxylin and eosin, and examined by light microscopy.

Plasma Analysis

Rats (250–275 8) anesthetized with ketamine-HCl (100 mg/ml at 1.5 ml/kg, i.p.) and xylazine (4 mg/ml at 4 mg/kg, i.p.), were implanted with a silastic catheter into the right jugular vein. Blood was withdrawn (0.5 cc) before implantation and at timed intervals after administration via the indwelling central venous cannulae. Plasma was extracted with an equal volume of HPLC grade methanol Fischer Scientific, Pittsburgh, Pa.), centrifuged (10,000×g) and the methanol phase filtered (0.2 $\mu$m nylon syringe type, Rainin, Woburn, Mass.) prior to HPLC analysis. The HPLC reliably quantified bupivacaine. concentrations in the plasma methanol extraction phase down to 10 ng/ml. The bupivacaine standards used for blood plasma analyses were added to plasma aliquots prior to methanol extraction. The peak matching the standard bupivacaine peak's retentions time was verified in plasma samples by doping with bupivacaine.

Statistics

Data were analyzed using linear regression tests, ANOVA, Chi Square tests and Wilcoxon rank-sum tests, where appropriate.

EXAMPLE 3

Prolonged Anesthesia with Microspheres Loaded with Local Anesthetic Agent and Glucocorticoid Since implantable devices require surgery to use, it is more desirable to make microspheres (ms) which can be injected. However, in order to obtain sensory or motor blockade or anesthesia effect for greater than one day, it was necessary to add dexamethasone (D) to microspheres. Addition of 0.05% D prolonged blockade or anesthesia effect by five to fourteen fold.

Methods and Material

Abbreviations include PLGA, poly-glycolic acid; $CH_2Cl_2$, methylene chloride; dpm, disintegrations per minute; cpm, counts per minute; rpm, revolutions per minute.

The non-radioactive polymer microspheres (Ms) used in this study were supplied by Medisorb, Cincinnati, Ohio. The PLGA 65:35 (Lot. No. S2170 Si177, Mw 130,000) was supplied by Medisorb, Cincinnati, Ohio. Tritium labeled dexamethasone was obtained from Amersham (specific activity 9.24×10$^{10}$ dpm/$\mu$mole) Bupivacaine free base was supplied by Purdue Frederick (Lot No. 32931) and dexamethasone was supplied by Sigma (Lot No. 34H0502). Trisma base was supplied by Sigma (Lot No. 64H5732). Dulbecco's phosphate-buffered saline was supplied by Gibco, Md. (Lot No. 14N5447). (2.68 KCL mM\L, 1.47 $KH_2PO_4$ mM\L, 547.5 NaCl mM\L, 9.50 mM\L $NaHPO_4$). The suspension media used in the in vivo experiments was supplied by Medisorb and consisted of 0.5% w\v sodium carboxymethylcellulose (medium viscosity) and 0.1% w\v Tween 80. A Coulter® Multisizer II, Coulter Electronics Ltd., Luton, England was used to determine the mass median diameter of the microspheres.

Polymer synthesis and Local Anesthetic Incorporation

The radiolabeled microspheres were formulated by a single emulsion technique, using an evaporation process. Two types of radiolabeled microspheres were formulated, one which contained 75% w/w unlabeled bupivacaine and 0.05% w/w tritium labeled dexamethasone and the other contained 0.05% w/w unlabeled dexamethasone and 75% w/w tritium labeled bupivacaine. The microspheres which contained tritium labeled dexamethasone were prepared as follows: an aliquot of dexamethasone containing 8×10$^6$ disintegrations per minute (dpm) was added to 100 $\mu$ls of a solution of 5 mg of unlabeled dexamethasone in 5 mls of ethanol. The sample was dried under a stream of nitrogen for one hour and 50 mg of PLGA 65:35 and 150 mg of bupivacaine free base in 1 ml of $CH_2Cl_2$ were added. The tube was vortexed for 1 minute at 2000 rpm on a Fisher Scientific Touch Mixer, Model 232. Then 1 ml of 0.3% polyvinylalcohol in 100 Mm Trisma® (tris(hydroxymethyl) amino methane) base (pH adjusted to 8.4) was added, and an emulsion formed by vortexing for 45 seconds. The emulsion was then poured into 100 mls of 0.1% polyvinylalcohol in 100 Mm Trisma® base. The $CH_2Cl_2$ was removed from the microspheres using a rotary evaporator under vacuum at 31° C. for 20 minutes. After 2–3 minutes bubbles formed, indicating that the organic solvent was being removed. The microspheres were sieved through a series of stainless steel sieves of pore sizes 140 $\mu$m, 60 $\mu$m and 20 $\mu$m (Newark Dire Co.). Those microspheres which were less than 20 and greater than 140 microns in diameter were discarded. The microspheres which fell in the size range 20 $\mu$m to 140 $\mu$m were centrifuged at 4000 rpm for 5 minutes rinsed with buffer and centrifuged again. The microspheres were then frozen in liquid nitrogen and lyophilized overnight. The microspheres were examined before and after solvent a removal using an American Optical One–Ten fight microscope to ensure that no leaching of the drug took place. If leaching did occur, the bupivacaine crystallized and could be seen even at 10× using a light microscope.

The microspheres which contained tritium labeled bupivacaine were, formulated as described above with the following exceptions: An aliquot of radiolabeled bupivacaine consisting of 9×10$^6$ dpm was added to 150 mg of unlabeled bupivacaine free base. The solution was then vortexed to ensure homogeneous mixing of labeled and unlabeled bupivacaine. The ethanol was then removed under a stream of nitrogen for 1 hour. Upon removal of the ethanol, 50 mg of PLGA 65:35 and 100 $\mu$l from a solution dexamethasone 1 mg/ml in ethanol was added. Thereafter, the protocol was the same as that used to formulate microspheres which contained radiolabeled dexamethasone.

In order to determine the drug content, 5 mg of microspheres were dissolved in 2 mls of $CH_2Cl_2$ and the local anesthetic concentration determined by U.V. spectroscopy. The absorbance at 272 nm was read and compared to a calibration curve of known amounts (0 to 2.5 mg/ml) of bupivacaine free base dissolved in $CH_2Cl_2$.

In Vitro Release studies

Unlabeled Microspheres 5 mg of microspheres were weighed out and 2mls of Dulbecco's phosphate-buffered saline was added. The pH of the buffer was adjusted to 7.4; and 0.1% sodium aside was added as an antimicrobial agent. The buffer was changed at 0.5, 2, 6, 12, and 24 hours and once daily thereafter. The amount of bupivacaine free base in the buffer was determined using a Hewlett Packard 8452 Diode Array Spectrophotometer at 272 nm. Duplicates from each batch of microspheres were assayed. Release media incubated with control microspheres which did not contain bupivacaine showed insignificant absorbance at 272 nm.

Labeled Microspheres

The procedure used to determine the in vitro release of both bupivacaine and dexamethasone is the same as that used for non-radiolabeled microspheres, except that the amount of radiolabeled compound released into the buffer was determined by adding 17 mls of Ecolume® scintillation fluid to 2 mls of buffer. The total number of counts was determined using a LKB Wallac 1214 Rackbeta Liquid Scintillation Counter. The efficiency, (the counts per minute/disintegration per minute), of the counter was determined to be 51%. Five replications of each set of radiolabeled microspheres were used.

Preparation of Microsphere Suspensions for Injection and In Vivo Testing

The dose used varied between 50 and 450 mg of drug/kg of rat, and 0.6 mls of injection vehicle was used for each injection. The injection vehicle consisted of 0.5% w/w sodium carboxy methyl cellulose and 0.1% w/w Tween 80 in water. The microspheres in the suspending media were vortexed at maximum speed for two minutes prior to injection. The injection was performed by locating and injecting slightly below and proximal to the greater trochanter. Rats were anesthetized with halothane 2–3% inspired concentration in oxygen during injections, at least five rats were used to. test each formulation.

Testing for Sciatic Nerve Anesthesia

Male Sprague-Dawley Charles River rats weighing between 200 and 350 grams were used to determine the duration of the blockade or anesthesia effect obtained with each of the different microsphere formulations tested. They were handled daily and habituated to the testing paradigm prior to exposure to local anesthetic injections. Sensory and motor blockade or anesthesia effect were examined as described above. The duration of the sensory blockade or anesthesia effect was determined as the length of time for which the latency was greater than or equal to 7 seconds.

In addition to sensory testing, motor testing was performed at each time point to examine the rat's ability to hop and to place weight on its hind leg. Animals were handled and cared for according to institutional, state, and federal regulation, and according to the guidelines of the International Association for the Study of Pain, Seattle, Wash.

Results

Microsphere morphology

Using the preparative procedures outlined above, smooth, spherical, mechanically stable microspheres were produced without significant quantities of crystalline bupivacaine leaching out the microspheres. When the drug leached out of the microspheres into the aqueous solution, it was in the form of long crystals, approximately 30 $\mu$m in length and was visible by light microscopy. Comparison of PLGA 65:35 microspheres loaded with 75% bupivacaine and 0.05% dexamethasone formulated by solvent-removal using a vacuum at 40° C. with those formulated by stirring the microspheres at room temperature and pressure, for three hours until the organic solvent evaporated, showed no significant differences. Increasing the rate of removal of the organic solvent using heat and vacuum reduced the rate of leaching of bupivacaine out of the microspheres from, e.g., about 40% to about 2%.

In vitro release kinetics

The in vitro results showed that the bupivacaine was released from the microspheres in a controlled manner. In general, between 24–40% of the bupivacaine was released in the first 24 hours, and approximately 7% released daily thereafter. Approximately 90% of the bupivacaine was released after 5–8 days. The presence of dexamethasone in the microspheres did not significantly affect the in vitro release rates of bupivacaine and the in vitro results cannot account for the prolongation of blockade or anesthesia effect, due to the presence of dexamethasone, observed in vivo.

Figure 1A:
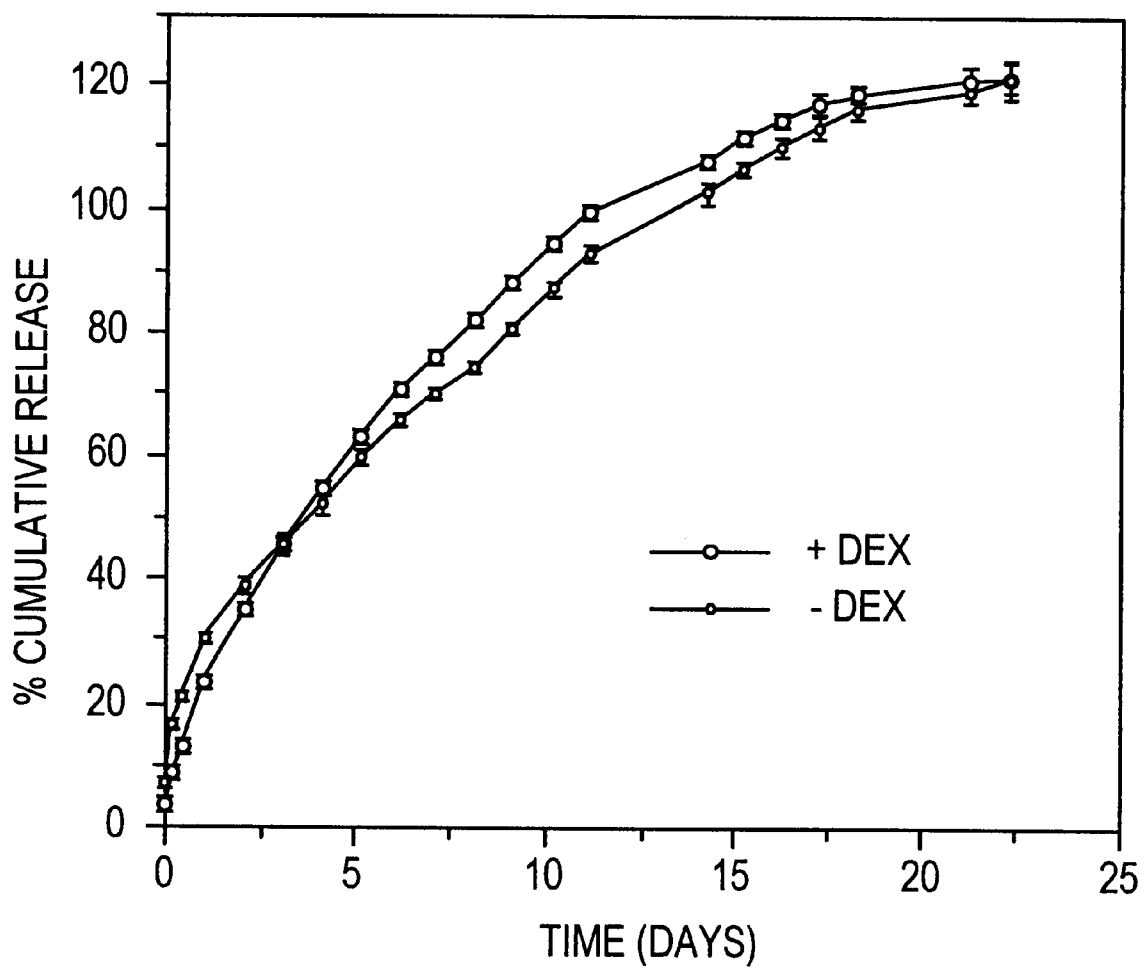
FIG. 1A is a graph of percent cumulative release of bupivacaine versus time (days), in vitro, for two formulations of polylactic acid-glycolic acid 75:25, one PLGA microsphere formulation with dexamethasone (open circle) and without dexamethasone (o pen square) 0.05%.

FIG. 1A compares the rates of in vitro release of bupivacaine from PLGA 75:25 microspheres loaded with 75% bupivacaine containing dexamethasone with those which did not contain dexamethasone. Bupivacaine is released at similar rates in both cases, so the presence of dexamethasone did not influence the rate of diffusion of bupivacaine out of the polymer microspheres.

In addition in vitro results obtained from release studies on microspheres containing radiolabeled drug confirms that dexamethasone was incorporated into the microspheres and was released at approximately the same rate as bupivacaine (data not shown). In FIG. 2, the percent cumulative release of bupivacaine versus time was overlaid for two different detection techniques, U.V. spectroscopy and scintillation counting. The two graphs paralleled each other, verifying the accuracy of the two different detection methods.

The in vitro release of bupivacaine from PLGA 50:50, PLGA 65:35, PLGA 75:25 and PLA are shown in FIG. 6. Note that PLA immediately (uncontrollably) releases the bupivacaine and that 75:25 and 65:35 show similar controlled release rates. FIG. 7 compares the percent cumulative release of bupivacaine from microspheres when the pH of the buffer media was 6, 7.4 and 8. The rate of release of bupivacaine was higher at pH 6 than at pH 7:4 or 8, because bupivacaine has a greater ionized fraction and greater aqueous solubility at pH 6 than at pH 7.4 or pH 8. At about day 10, pH 7.4 bupivacaine release stopped, but the release of bupivacaine at pH 8 continued past 80% cumulative release. The excursion above the 100% cumulative release mark reflects the cumulative nature of the standard error when the data is presented in this manner.

Radiolabeled microspheres

When microspheres loaded with unlabeled bupivacaine and radio labeled dexamethasone were prepared, the yield (weight of microspheres/weight of bupivacaine +weight of polymer) was 45%. The bupivacaine content was determined to be 75±1%. When microspheres loaded with unlabeled dexamethasone and radiolabeled bupivacaine were prepared, the yield was 50%, and the bupivacaine content was 73±2%. FIG. 1A confirms that dexamethasone was incorporated into the microspheres and that both substances were released at similar release rates. The comparison of U.V. spectroscopy and scintillation counting used to monitor the in vitro release of unlabeled and radio labeled bupivacaine, respectively, show that essentially the same release rate was measured using the two techniques (FIG. 2).

Rat Sciatic Nerve Anesthesia In Vivo

Figure 1B:
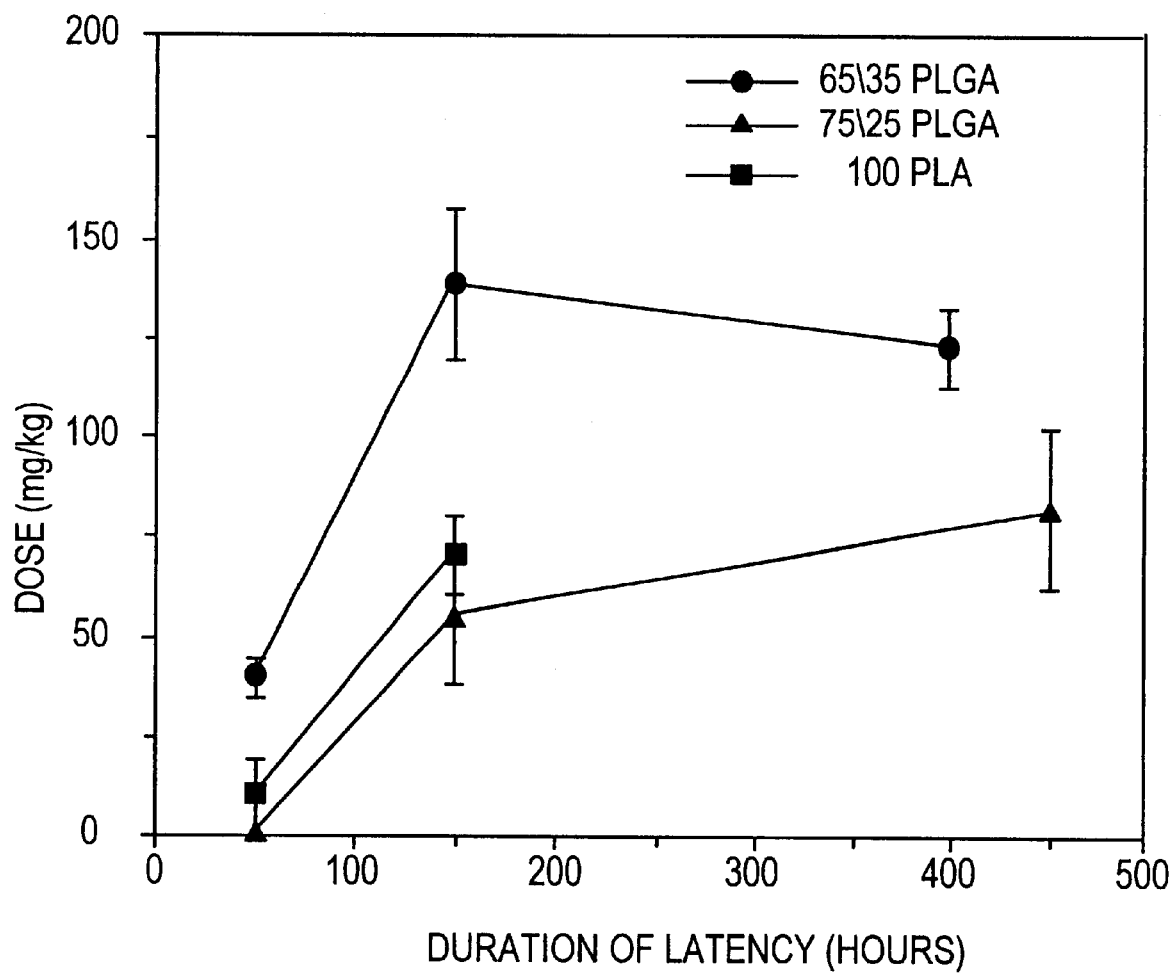
FIG. 1B is a graph of bupivacaine dose verses the duration of sensory latency (hours), in animals treated with microspheres containing bupivacaine 75% (w/w) and 0.05% dexamethasone prepared from 100 polylactic acid ("PLA"

In order to determine the toxic response of the rats to various microsphere doses, the rats were injected with concentrations ranging from 50 to 450 mg of bupivacaine/kg of rat for each type of polymer. The corresponding plots of dose verses duration of latency are shown in FIG. 1B. FIG. 1B shows that among PLA 100, PLGA 75:25 and PLGA 65:35, the later two provided the longest duration of latency. No systemic toxicity, excessive sluggishness or death was observed even at the highest doses. FIGS. 4A–4D compare the duration of sensory blockade or anesthesia effect for groups of rats injected with bupivacaine-loaded PLA 100, PLGA 75:25, PLGA 65:35 and PLGA 50:50 microspheres, respectively, with and without incorporated dexamethasone. In each case, the presence of dexamethasone in the microspheres resulted in a 6–13 fold increase in the duration of blockade or anesthesia effect. Mean sciatic anesthesia durations among treatment groups varied from 65±3 to 134±13 hours for microsphere formulations which contained dexamethasone. Control groups receiving injections of polymer microspheres containing no drug or dexamethasone or containing dexamethasone alone showed no sensory or motor blockade or anesthesia effect. PLGA 65:35 microspheres which contained 0%, 0.005% and 0.05% dexamethasone, at a dose of 150 mg/kg of rat, provided 8, 50 and 170 hours of sensory latency, respectively, as shown in FIG. 3A.

Experiments confirmed that 65:35 PLGA polymers were preferable to either 75:25 PLGA or 100% PLA, both in terns of (1) the reliability, intensity and duration of sciatic anesthesia, (2) each of dispersal and injectability. A blockade or anesthesia effect of 30–40 hours was observed with PLGA 50:50 over the PLGA 65:35 microspheres, indicating no advantage. The optimum dose and formulation was determined to be about 150 mg of drug/kg of rat of PLGA 65:35 microspheres loaded with 75% bupivacaine and 0.05% dexanethasone, as this was the lowest dose which resulted in the longest duration of blockade or anesthesia effect.

The presence of 0.05% dexamethasone in microspheres significantly prolonged the duration of sciatic anesthesia. That is, the blockade or anesthesia effect obtained using microspheres which contained 0.05% dexamethasone was up to 13 fold long than the blockade or anesthesia effect obtained using the corresponding microspheres which did not contain any dexamethasone. The 65:35 PLGA provides optimum duration of latency over 75:25 PLGA and 100PLA microspheres loaded with bupivacaine and dexamethasone as shown in FIG. 1B. This is confirmed by FIG. 3A, which shows a dose-response effect on latency between 0.05% dexamethasone and 0.005% dexamethasone. Analogous results were obtained for motor blockade or anesthesia effect versus time as shown by FIG. 3B. Mean sciatic anesthesia durations among treatment groups varied from 65±3 to 134±13 hours for microsphere formulations which contained dexamethasone. Control groups receiving injections of polymer microspheres containing no drug or dexamethasone or containing dexamethasone alone showed no sensory or motor blockade or anesthesia effect. It was determined that 150 mg of bupivacaine/kg of rat was the optimum dosage and no further prolongation of blockade or anesthesia effect was obtained by injecting a higher dose. The optimum formulation was determined to be 150 mg of bupivacaine/kg of rat in PLGA 65:35 microspheres which contained 75% bupivacaine and 0.05% dexamethasone (the mass median diameter was 70 µm, determined using a coulter counter). Using this formulation a 134 hour sciatic anesthesia was achieved.

EXAMPLE 4

Administration of Microspheres in Combination with Glucocorticoids in Solution

A model system was developed in which dexamethasone was dissolved in ethanol and an aliquot of known concentration was added to the suspending medium-which contained microspheres loaded with about 75% bupivacaine. Addition of dexamethasone to the suspending medium in concentrations ranging from 0.05% to 0.5% prolonged the duration of blockade or anesthesia effect obtained using bupivacaine microspheres.

This model system then permitted testing of a series of compounds over full concentration ranges for prolongation of sciatic blockade or anesthesia effect in vivo without the labor-intensive step of making a microsphere prep with each additive and each dose.

Various concentrations of additives were placed in the injection vehicle along with bupivacaine microspheres and tested for their ability to prolong blockade or anesthesia effect. This model allowed a number of different additives to be tested quickly and efficiently.

Dexamethasone was dissolved in ethanol and an aliquot of known concentration was added to the suspending medium which contained microspheres loaded with 75% bupivacaine. Addition of dexamethasone to the suspending medium in concentrations ranging from 0.05% to 0.5% prolonged the duration of blockade or anesthesia effect obtained using bupivacaine microspheres. Addition of 0.005% (w/w) bupivacaine did not result in a prolongation of the blockade or anesthesia effect obtained.

This model system then permitted testing of a series of compounds over full concentration ranges for prolongation of sciatic blockade or anesthesia effect in vivo without the labor-intensive step of making a microsphere prep with each additive and each dose.

Various concentrations of additives were placed in the injection vehicle along with bupivacaine microspheres and tested for their ability to prolong blockade or anesthesia effect. This model allowed a number of different additives to be tested quickly and efficiently.

Materials and Methods

Materials

The following polymer microspheres were formulated by solvent evaporation method (polymer molecular weight 130, 000), and supplied by Medisorb, Cincinnati, Ohio: 65:35 PLGA loaded with 75% bupivacaine, 65:35 PLGA loaded with 75% bupivacaine and 0.05% cholesterol. Estradiol, testosterone, betamethasone and dexamethasone were supplied by Sigma, St. Louis, Mo. Cholesterol was supplied by Aldrich, Milwaukee, Wis., hydrocortisone (Solu-Cortef®) and methylprednisolone was supplied by Upjohn Co., Kalamazoo, Mich. Epinephrine was supplied by ElkinsSinn, Inc., New Jersey, Ketorolac. The bupivacaine in saline (Sensorcaine®) was supplied by Astra Pharmaceutical, Mass.

Preparation of the Suspension and In vivo Testing

Male Sprague-Dawley Charles River Rats, weighing between 200 and 350 grams were used to test the ability of each additive to prolong blockade or anesthesia effect. 150 mg of bupivacaine per kg of rat and a known concentration of each of the additives were placed in 0.6 mls of injection vehicle (5 g/L medium molecular weight carboxymethylcellulose, 1 g/L Tween 80). If the additive was a solid, it was dissolved in ethanol and aliquots which varied in concentrations from 0.0220 mg/kg of rat, and added to the injection fluid. If the additive was in liquid form, it was added directly to the injection fluid. The microsphere/additive mixture was vortexed (Scientific Industries Vortex Genie®) at maximum speed for three minutes prior to injection. The injection was performed while the rats were under general anesthetic, by locating the greater trochanter and injecting slightly below and proximal to it. At least five rats were used in each test.

Sensory blockade or anesthesia effect was examined using art-known techniques. In addition, motor tests were performed at each time point to examined each rat's ability to hop and to place weight on it's hind leg by art-known techniques. Each leg was tested three times, and the latency of the contralateral leg was tested to provide a control. The animals were handled and cared for according to institution, state, and federal regulations.

Results

Table 1 shows the duration of blockade or anesthesia effects obtained when dexamethasone alone, liquid bupivacaine alone and a combination of liquid bupivacaine and two different concentrations of liquid dexamethasone were tested in vivo. Table 2 shows the duration of blockade or anesthesia effects obtained when glucocorticoids, steroids and non-steroidal anti-inflammatories (NSAIDs) were placed in the injection fluid along with bupivacaine microspheres. Dexamethasone in aqueous solution did not produce any sciatic blockade or anesthesia effect, nor did it prolong blockade or anesthesia effect when co-administered with bupivacaine in solution (Table 1). Dexamethasone and betamethasone were approximately equivalent in augmenting motor blockade or anesthesia effect (FIG. 5B) but dexamethasone was optimal for sensory blockade or anesthesia effect (FIG. 5A). The sensory blockade or anesthesia effect results parallel those obtained from motor blockade or anesthesia effect testing. These results are confirmed by FIG. 5C showing a plot of the duration of sensory block (hours) versus log concentration of dose of additives placed in the injection fluid (mg/kg).

In addition, 0.3 mg/kg of cholesterol was incorporated into bupivacaine loaded microspheres, but its presence did not result in a prolongation of blockade or anesthesia effect when compared to the blockade or anesthesia effect obtained from bupivacaine microspheres.

TABLE 1

Liquid bupivacaine and the following additives were injected to determine if dexamethasone in the presence of liquid bupivacaine would prolong blockade or anesthesia effect.

| NO. OF RATS | CONC. BUPIVACAINE (mg/kg RAT) | CONC. DEXAMETHASONE (mg/kg RAT) | LENGTH OF Blockade or anesthesia effect (HOURS) |
|---|---|---|---|
| 5 | 3 | — | 2–3 |
| 5 | — | 0.16 | 0 |
| 5 | 3 | 0.16 | 2–3 |
| 5 | 3 | 1.6 | 2–3 |

FIG. 5A shows that bupivacaine microspheres in the presence of dexamethasone provides a sensory blockade or anesthesia effect where the initial blockade or anesthesia effect latency of 12 seconds falls to a latency of about 7 seconds after 50 hours and about 2.5 seconds after 100 hours. Betamethasone provided a similar duration of sensory blockade or anesthesia effect. Analogous results were obtained (FIG. 5B) for motor blockade or anesthesia effect.

Results

The results are shown in Table 2 as follows:

TABLE 2

| Number of rats | Additives (mg/Kg rat) | Sensory block (hours) | Motor block (hours) |
|---|---|---|---|
| 11 | — | 6.0 ± 1.0 | 5.0 ± 0.3 |
| 7 | Dexamethasone (0.14) | 47.0 ± 8.0 | 38.0 ± 5.0 |

TABLE 2-continued

| Number of rats | Additives (mg/Kg rat) | Sensory block (hours) | Motor block (hours) |
|---|---|---|---|
| 5 | Dexamethasone (0.02) | 17.0 ± 11.0 | 19.0 ± 8.0 |
| 5 | Dexamethasone (2.0) | 36.0 ± 19.0 | 34.0 ± 12.0 |
| 5 | Betamethasone (2.0) | 44.0 ± 13.0 | 39.0 ± 11.0 |
| 5 | Betamethasone (0.8) | 46.0 ± 7.0 | 39.0 ± 5.0 |
| 5 | Betamethasone (0.25) | 36.0 ± 10.0 | 38.0 ± 11.0 |
| 5 | Betamethasone (0.032) | 19.0 ± 4.0 | 15.0 ± 4.0 |
| 5 | Methylprednisolone (20) | 34.0 ± 11.0 | 33.0 ± 9.0 |
| 7 | Methylprednisolone (2.1) | 28.0 ± 6.0 | 28.0 ± 5.0 |
| 5 | Methylprednisolone (0.1) | 20.0 ± 5.0 | 13.0 ± 4.0 |
| 7 | Hydrocortisone (0.1) | 10.0 ± 3.0 | 10.0 ± 3.0 |
| 5 | Hydrocortisone (1.25) | 15.0 ± 5.0 | 16.0 ± 3.0 |
| 5 | Hydrocortisone (10) | 36.0 ± 10.0 | 31.0 ± 8.0 |
| 5 | Ketoralac (2.0) | 6.0 ± 0.7 | 7.0 ± 0.4 |
| 5 | Ketoralac (6.3) | 8.0 ± 2.0 | 10.0 ± 4.0 |
| 4 | Estradiol (1.25) | 8.0 ± 1.0 | 9.0 ± 2.0 |
| 4 | Estradiol (0.125) | 11.0 ± 6.0 | 12.0 ± 6.0 |
| 8 | Cholesterol (0.1) | 4.0 ± 0.4 | 4.0 ± 1.0 |
| 5 | Cholesterol (3.1) | 8.0 ± 3.0 | 5.0 ± 1.0 |
| 5 | Testosterone (1.7) | 15.0 ± 5.0 | 15.0 ± 5.0 |
| 5 | Testosterone (1.0) | 7.0 ± 2.0 | 6.0 ± 1.0 |
| 4 | Progesterone (2.0) | 8.0 ± 1.0 | 6.0 ± 1.0 |
| 5 | Epinephrine (0.01) | 12.0 ± 6.0 | 12.0 ± 4.0 |
| 5 | Epinephrine (0.1) | 14.0 ± 5.0 | 11.0 ± 3.0 |

The results demonstrate that dexamethasone does not produce sciatic blockade or anesthesia effect by itself in solution, nor does it prolong blockade or anesthesia effect from bupivacaine in solution. Addition of dexamethasone in solution with bupivacaine in solution did not prolong blockade or anesthesia effect relative to bupivacaine in solution alone. The prolonged blockade or anesthesia effect previously observed seemed to require the presence of bupivacaine in microspheres. The data confirm that glucocorticoid produce a block-prolonging effect proportioned to their potency (as glucocorticoids).

It can be seen that:
i. High potency glucocorticoids such as betamethasone also produce prolongation of blockade or local anesthesia effect up to about 45 hours in duration.
ii. Intermediate potency glucocorticoids such as methylprednisolone produce intermediate degrees of blockade or sensory effect prolongation.
iii. Weaker glucocorticoids such as hydrocortisone produce mild, but statistically significant prolongation of blockade or anesthesia effect.
iv. The weaker prolongation of blockade or anesthesia effect by hydrocortisone cannot be made as effective as dexamethasone by further increasing its concentration in the suspending medium.
v. Estrogen has no blockade-prolonging effect. Testosterone showed a mild prolongation of blockade or anesthesia effect (testosterone is a relatively weak hormone compared with synthetic analogues);
vi. NSAIDs and epinephrine did not substantially prolong blockade or sensory effect. Epinephrine in the doses used (0.05%. in the suspending medium) produced considerable systemic toxicity, but no deaths.

EXAMPLE 5

Restoration of Local Anesthesia by Dexamethasone

Male Sprague-Dawley Charles River rats, weighing between 200 and 350 grams were used to confirm the ability of dexamethasone, a glucocorticosteroid, to reestablish local anesthesia when locally administered after a bupivacaine-microsphere induced local anesthesia was waning.

Rats were injected into or adjacent to the sciatic nerve with PLGA 65:35 controlled release microspheres loaded with bupivacaine (about 75% percent loading).

Sensory latency was determined by the hot plate foot withdrawal method described above. During the first 6 hours after injection, the mean hot plate latency fell from 12 sec to about 5 sec. At 6 hours the test animals were injected at original site with 0.032 mg/kg of dexamethasone. This produced an immediate restoration of sensory anesthesia, as confirmed by the hot plate sensory latency, that moved up to about 11 sec. FIG. 8A, closed squares). Anesthetized control animals that received 6 hour injections of vehicle without. dexamethasone (FIG. 8A, closed. triangles) and no second injection (FIG. 8A, closed circles) showed no such restoration of sensory anesthesia.

The same procedure was repeated with the measurement of motor blockade or anesthesia effect, with the same results. Dexamethasone (0.5%) produced a rapid restoration of the motor anesthesia (FIG. 8B, solid circles). Previously anesthetized animals receiving 6 hour injections of vehicle without dexamethasone (FIG. 8B, open circles) and receiving no further injections (FIG. 8B, open squares) showed a continued decline in motor anesthesia.

CONCLUSION

The present invention is not to be limited in scope by the specific embodiments described herein. Indeed, various modifications of the invention in addition to those described herein will become apparent to those skilled in the art from the foregoing description. Such modifications are intended to fill within the scope of the claims. Various publications are cited herein, the disclosures of which are incorporated by reference in their entireties.

What is claimed is:

1. A method for providing prolonged local analgesia at a site in a patient in need thereof, comprising
   administering a local anesthetic in controlled release form at a site in a patient at which local analgesia is desired, and thereafter
   administering at the site a glucocorticosteroid agent, in an amount effective to reactivate or prolong local analgesia, said glucocorticosteroid agent being administered at least one hour after said local anesthetic is administered.

2. The method according to claim 1, wherein said local anesthetic is administered by a method selected from the group consisting of topical application, implantation, infiltration, injection, infusion and any combination thereof, at or adjacent to the site requiring local analgesia.

3. The method according to claim 1, wherein said glucocorticosteroid agent is administered by a method selected from the group consisting of topical application, implantation, infiltration, injection, infusion and systemic administration and any combination thereof, at or adjacent to the site requiring reactivated analgesia.

4. The method of claim 1, wherein at least a portion of said glucocorticosteroid agent is administered at a time period ranging from about 1 to about 6 hours after said previous local anesthetic was administered.

5. The method of claim 1 wherein at least a portion of said glucocorticosteroid is in controlled release form.

6. The method of claim 5 further comprising preparing said controlled release form as a plurality of microspheres comprising said glucocorticosteroid, suspending said microspheres in a pharmaceutically acceptable medium for injection, and injecting said microspheres at the site requiring reactivated analgesia.

7. The method of claim 1 wherein said local anesthetic is selected from the group consisting of bupivacaine, ropivacaine, dibucaine, procaine, chloroprocaine, prilocaine, mepivacaine, etidocaine, tetracaine, lidocaine, xylocaine, and mixtures and salts thereof.

8. The method of claim 7 wherein the local anesthetic is bupivacaine.

9. The method of claim 1 wherein the reactivated local analgesia ranges in duration from about 1.1 to about 14 fold or more of the duration of local analgesia induced by controlled release local anesthetic without restoration.

10. The method of claim 1, wherein the reactivated local analgesia ranges in duration from about 1 to about 72 hours, measured from the time of administration of said effective amount of said glucocorticosteroid agent.

11. The method of claim 1 wherein the glucocorticosteroid is selected from the group consisting of dexamethasone, cortisone, prednisone, hydrocortisone, beclomethasone dipropionate, betamethasone, flunisolide, methylprednisone, paramethasone, prednisolone, triamcinolone, alclometasone, amcinonide, clobetasol, fludrocortisone, diflorasone diacetate, fluocinolone acetonide, fluocinonide, fluorometholone, flurandrenolide, halcinonide, medrysone and mometasone and pharmaceutically acceptable mixtures thereof and salts thereof.

12. The method of claim 11 wherein the glucocorticosteroid is dexamethasone.

13. The method of claim 8 wherein the bupivacaine is administered in a dose ranging from about 0.5 to about 1000 mg at a site in the patient.

14. The method of claim 1, wherein said local anesthetic in controlled release form comprises microparticles that are suspended in a medium that is pharmaceutically acceptable for administration by a method selected from the group consisting of injection, instillation and topical application.

15. The method of claim 1, wherein the local anesthetic in controlled release form comprises a polymer selected from the group consisting of polyanhydrides, copolymers of acid and glycolic acid, poly(lactic) acid, poly(glycolic) acid, polyesters, polyorthoesters, proteins, and polysaccharides.

16. The method of claim 1, wherein the local anesthetic is incorporated into said controlled release form at a percent loading of 0.1% to 90% by weight.

17. The method according to claim 1, wherein said glucocorticosteroid agent is administered at a time ranging from about 4 to about 24 hours after said local anesthetic was administered.

18. The method according to claim 14, wherein said microparticles are microspheres ranging in size from about 5 microns to about 200 microns in diameter.

19. The method according to claim 1 wherein said local anesthetic is incorporated into said controlled release form at a percent loading of about 75% by weight.

20. The method of claim 15 wherein said local anesthetic is incorporated into microspheres in an amount from about 45% to about 70% by weight, the copolymer being PLGA in a 50:50 ratio, said copolymer having a molecular weight ranging from about 5000 to about 200,000.

21. The method according to claim 17, wherein said local anesthetic is bupivacaine.

22. The method of claim 1, wherein said controlled release form is liposomes.

23. The method of claim 1, wherein said local anesthetic in controlled release form comprises microcapsules.

24. The method of claim 1 wherein said local anesthetic is bupivacaine and said glucocorticosteroid is dexamethasone.

25. A method for providing prolonged local analgesia at a site in a patient in need thereof, comprising
administering bupivacaine or a salt thereof in controlled release form at a site in a patient at which local analgesia is desired, and thereafter
administering at the site dexamethasone or a salt thereof, in an amount effective to reactivate or prolong local analgesia, said dexamethasone or salt thereof being administered at least one hour after said bupivacaine or a salt thereof was administered.

26. The method of claim 25 wherein said bupivacaine or salt thereof in controlled release form comprises microcapsules.

27. The method of claim 25 wherein said bupivacaine or salt thereof in controlled release form comprises microspheres.

28. The method of claim 25 wherein said bupivacaine or salt thereof in controlled release form comprises a polymer selected from the group consisting of polyanhydrides, copolymers of lactic acid and glycolic acid, poly(lactic) acid, poly(glycolic) acid, polyesters, polyorthoesters, proteins, polysaccharides, and combinations thereof.

29. The method of claim 25 wherein said bupivacaine or salt thereof in controlled release form is administered in the form of
a plurality of substrates in a pharmaceutically acceptable medium for injection, said substrates comprising said bupivacaine or salt thereof and an effective amount of a biocompatible, biodegradable controlled release material comprising a polymer selected from the group consisting of polyanhydrides, copolymers of lactic acid and glycolic acid, poly(lactic) acid, poly(glycolic) acid, polyesters, polyorthoesters, proteins, polysaccharides and combinations thereof.

30. The method of claim 27 wherein said microspheres are incorporated into a pharmaceutically acceptable solution or suspension for injection.

31. The method of claim 27, wherein said microspheres are in a reconstitutable form.

32. The method of claim 31 further comprising reconstituting said microspheres using a pharmaceutically acceptable solution or suspension for injection.

33. The method of claim 15 wherein said local anesthetic is incorporated into microspheres in an amount from about 60% to about 85% by weight, the copolymer being PLGA in a 50:50 ratio, said copolymer having a molecular weight ranging from about 5000 to about 200,000.

34. The method of claim 15 wherein said local anesthetic is incorporated into microspheres in an amount from about 60% to about 85% by weight, the copolymer being PLGA in a 65:35 ratio, said copolymer having a molecular weight ranging from about 5000 to about 200,000.

35. The method of claim 15 wherein said local anesthetic is incorporated into microspheres in an amount from about 60% to about 85% by weight, the copolymer being PLGA in a 75:25 ratio, said copolymer having a molecular weight ranging from about 5000 to about 200,000.

36. The method of claim 15 wherein said local anesthetic is incorporated into microspheres in an amount from about 60% to about 85% by weight, the copolymer being PLGA in a 85:15 ratio, said copolymer having a molecular weight ranging from about 5000 to about 200,000.

37. A method for providing local anesthesia or analgesia at a site in a patient in need thereof, comprising administering an amount of a local anesthetic effective to induce local anesthesia or analgesia at a site in a patient and an amount of a glucocorticosteroid effective to reactivate or prolong said local anesthesia or analgesia, said local anesthetic and said glucocorticosteroid being provided in controlled release form such that an amount of said glucocorticosteroid effective to reactivate or prolong the desired local anesthesia or analgesia is provided at the site at least one hour after the local anesthetic has been administered.

38. The method of claim 37, wherein the amount of said glucocorticosteroid that is effective to reactivate or prolong the desired local anesthesia or analgesia is provided from about one hour to about 72 hours after the local anesthetic has been administered.

39. The method of claim 37, wherein the amount of said glucocorticosteroid that is effective to reactivate or prolong the desired local anesthesia or analgesia is provided from about one hour to about 24 hours after the local anesthetic has been administered.

40. The method of claim 37, wherein the amount of said glucocorticosteroid that is effective to reactivate or prolong the desired local anesthesia or analgesia is provided from about one hour to about 6 hours after the local anesthetic has been administered.

41. The method of claim 37, wherein the local anesthetic is bupivacaine.

42. The method of claim 37, wherein the glucocorticosteroid is dexamethasone.

43. The method of claim 37, wherein said controlled release form comprises a plurality of substrates in a pharmaceutically acceptable medium for injection, said substrates comprising a local anesthetic and an effective amount of a biocompatible, biodegradable controlled release material comprising a polymer selected from the group consisting of polyanhydrides, copolymers of lactic acid and glycolic acid, poly(lactic) acid, poly (glycolic) acid, polyesters, polyorthoesters, proteins, polysaccharides and combinations thereof, said biocompatible, biodegradable controlled release material being capable of prolonging the release of said local anesthetic from said substrates in vitro.

44. The method of claim 37, wherein said controlled release form is liposomes.

45. The method of claim 43, wherein said plurality of substrates comprises microcapsules, microspheres or microparticles.

46. The method of claim 37 wherein said local anesthetic is incorporated into said controlled release form at a percent loading of about 30% to about 90% by weight.

47. The method of claim 37, wherein said local anesthetic is incorporated into said controlled release form at a percent loading of about 60% to about 85% by weight.

48. The method of claim 40, wherein the glucocorticosteroid is dexamethasone.

49. The method of claim 37, wherein said controlled release form comprises an outer layer of controlled release local anesthetic agent coated on a substrate comprising a glucocorticosteroid in controlled release form.

50. The method of claim 37, wherein the controlled release form comprises a mixture of microspheres formed of polymers having different release rates.

51. A method for reactivating a previously induced local anesthesia or analgesia, comprising administering a pharmaceutically acceptable composition comprising an effective amount of a local anesthetic and a glucocorticosteroid agent in an amount effective to prolong local anesthesia or analgesia at a site in a patient in need thereof, and thereafter administering a further dose of glucocorticosteroid effective to reactivate the anesthesia or analgesia, said further dose of glucocorticosteroid agent being administered at least one hour after said local anesthetic is administered.

52. The method of claim 51, wherein the local anesthetic is bupivacaine.

53. The method of claim 51, wherein the glucocorticosteroid is dexamethasone.

54. The method of claim 51, wherein said local anesthetic is in controlled release form.

55. The method of claim 54, wherein said local anesthetic is administered in the form of
a plurality of substrates in a pharmaceutically acceptable medium for injection, said substrates comprising a local anesthetic and an effective amount of a biocompatible, biodegradable controlled release material comprising a polymer selected from the group consisting of polyanhydrides, copolymers of lactic acid and glycolic acid, poly(lactic) acid, poly (glycolic) acid, polyesters, polyorthoesters, proteins, polysaccharides and combinations thereof, said biocompatible, biodegradable controlled release material being capable of prolonging the release of said local anesthetic from said substrates in vitro.

56. The method of claim 54, wherein said controlled release form is liposomes.

57. The method of claim 55, wherein said plurality of substrates comprises microcapsules, microspheres or microparticles.

58. The method of claim 54 wherein said local anesthetic is incorporated into said controlled release form at a percent loading of about 30% to about 90% by weight.

59. The method of claim 54, wherein said local anesthetic is incorporated into said controlled release form at a percent loading of about 60% to about 85% by weight.

60. The method of claim 54, wherein said controlled release form comprises an outer layer of controlled release local anesthetic agent coated on a substrate comprising a glucocorticosteroid in controlled release form.

61. The method of claim 54, wherein the controlled release form comprises a mixture of microspheres formed of polymers having different release rates.

62. The method of claim 37, wherein the glucocorticosteroid is selected from the group consisting of dexamethasone, cortisone, prednisone, hydrocortisone, beclomethasone dipropionate, betamethasone, flunisolide, methylprednisone, paramethasone, prednisolone, triamcinolone, alclometasone, amcinonide, clobetasol, fludrocortisone, diflorasone diacetate, fluocinolone acetonide, fluocinonide, fluorometholone, flurandrenolide, halcinonide, medrysone and mometasone and pharmaceutically acceptable mixtures thereof and salts thereof.

63. The method of claim 51, wherein the glucocorticosteroid is selected from the group consisting of dexamethasone, cortisone, prednisone, hydrocortisone, beclomethasone dipropionate, betamethasone, flunisolide, methylprednisone, paramethasone, prednisolone, triamcinolone, alclometasone, amcinonide, clobetasol, fludrocortisone, diflorasone diacetate, fluocinolone acetonide, fluocinonide, fluorometholone, flurandrenolide, halcinonide, medrysone and mometasone and pharmaceutically acceptable mixtures thereof and salts thereof.

64. The method of claim 39, wherein said local anesthetic is selected from the group consisting of bupivacaine, ropivacaine, dibucaine, procaine, chloroprocaine, prilocaine, mepivacaine, etidocaine, tetracaine, lidocaine, xylocaine, and mixtures and salts thereof.

65. The method of claim 51, wherein said local anesthetic is selected from the group consisting of bupivacaine, ropivacaine, dibucaine, procaine, chloroprocaine, prilocaine, mepivacaine, etidocaine, tetracaine, lidocaine, xylocaine, and mixtures and salts thereof.

* * * * *